US011756716B2

United States Patent
Jang et al.

(10) Patent No.: US 11,756,716 B2
(45) Date of Patent: Sep. 12, 2023

(54) MAGNETIC FIELD CONTROL SYSTEM

(71) Applicant: IUCF-HYU (INDUSTRY-UNIVERSITY COOPERATION FOUNDATION HANYANG UNIVERSITY), Seoul (KR)

(72) Inventors: Gunhee Jang, Seoul (KR); Jaekwang Nam, Goyang-si (KR); Wonseo Lee, Yongin-si (KR); Bongjun Jang, Seoul (KR)

(73) Assignee: IUCF-HYU (INDUSTRY-UNIVERSITY COOPERATION, FOUNDATION HANYANG UNIVERSITY) Seoul (KR)

( * ) Notice: Subject to any disclaimer, the term of this patent is extended or adjusted under 35 U.S.C. 154(b) by 1250 days.

(21) Appl. No.: 16/324,165

(22) PCT Filed: Apr. 14, 2017

(86) PCT No.: PCT/KR2017/004070
§ 371 (c)(1),
(2) Date: Feb. 8, 2019

(87) PCT Pub. No.: WO2018/030610
PCT Pub. Date: Feb. 15, 2018

(65) Prior Publication Data
US 2019/0184545 A1    Jun. 20, 2019

(30) Foreign Application Priority Data

Aug. 10, 2016  (KR) .................. 10-2016-0101756
Sep. 21, 2016  (KR) .................. 10-2016-0120698
Sep. 30, 2016  (KR) .................. 10-2016-0126395

(51) Int. Cl.
A61K 35/12        (2015.01)
H01F 7/20         (2006.01)
(Continued)

(52) U.S. Cl.
CPC ............. *H01F 7/206* (2013.01); *A61B 1/005* (2013.01); *A61M 37/00* (2013.01); *B25J 5/00* (2013.01);
(Continued)

(58) Field of Classification Search
USPC ....................................... 700/245
See application file for complete search history.

(56) References Cited

U.S. PATENT DOCUMENTS 6,236,133 B1 * 5/2001 Nishikawa ............ H02K 29/03
                                                   310/179
6,311,082 B1 * 10/2001 Creighton, IV ....... A61B 34/73
                                                   600/407
(Continued)

FOREIGN PATENT DOCUMENTS

CN        1681448 A    10/2005
CN      101282677 A    10/2008
(Continued)

OTHER PUBLICATIONS

International Search Report of PCT/KR2017/004070 dated Jul. 21, 2017 [PCT/ISA/210].

*Primary Examiner* — Shawki S Ismail
*Assistant Examiner* — Lisa N Homza
(74) *Attorney, Agent, or Firm* — Sughrue Mion, PLLC

(57) ABSTRACT

A magnetic field control system according to an embodiment of the present invention may comprise: a structure forming part for forming a three-dimensional structure having an inner space; a magnetic field generating part for generating a magnetic field, the magnetic field generating part being
(Continued)

formed to extend from a predetermined position of the structure forming part and being disposed to face a target region defined in the inner space; and a power source part for supplying electric power to the magnetic field generating part.

11 Claims, 28 Drawing Sheets

(51) Int. Cl.
    *A61M 37/00*     (2006.01)
    *A61B 1/005*     (2006.01)
    *B25J 9/16*     (2006.01)
    *H01F 5/02*     (2006.01)
    *H01F 38/14*     (2006.01)
    *B25J 5/00*     (2006.01)
    *G05B 19/04*     (2006.01)
    *B25J 7/00*     (2006.01)
    *H01F 7/06*     (2006.01)
    *H01F 27/24*     (2006.01)
    *H01F 27/28*     (2006.01)
    *A61M 25/01*     (2006.01)

(52) U.S. Cl.
    CPC .. *B25J 7/00* (2013.01); *B25J 9/16* (2013.01); *B25J 9/1679* (2013.01); *G05B 19/04* (2013.01); *H01F 5/02* (2013.01); *H01F 7/064* (2013.01); *H01F 27/24* (2013.01); *H01F 27/28* (2013.01); *H01F 38/14* (2013.01); *A61M 25/0116* (2013.01); *A61M 25/0127* (2013.01)

(56) References Cited

U.S. PATENT DOCUMENTS

| | | | |
|---|---|---|---|
| 6,437,567 | B1 | 8/2002 | Schenck et al. |
| 2002/0185929 | A1* | 12/2002 | Jang .................. H02K 21/16 |
| | | | 310/210 |
| 2004/0019447 | A1 | 1/2004 | Shachar |
| 2013/0053619 | A1 | 2/2013 | McKenna et al. |
| 2013/0184526 | A1* | 7/2013 | Takizawa ........... A61B 1/00148 |
| | | | 600/109 |
| 2022/0122752 | A1* | 4/2022 | Jang .................. H01F 27/28 |

FOREIGN PATENT DOCUMENTS

| | | |
|---|---|---|
| JP | 2002-233575 A | 8/2002 |
| JP | 2004-283584 A | 10/2004 |
| JP | 2005-532878 A | 11/2005 |
| JP | 2007-160078 A | 6/2007 |
| JP | 2007-173580 A | 7/2007 |
| JP | 2012-501689 A | 1/2012 |
| JP | 2014-525290 A | 9/2014 |
| KR | 10-2009-0061974 A | 6/2009 |
| KR | 10-2009-0109818 A | 10/2009 |
| KR | 10-2010-0044396 A | 4/2010 |
| KR | 10-2010-0136206 A | 12/2010 |
| KR | 10-2011-0000779 A | 1/2011 |
| KR | 10-2013-0036273 A | 4/2013 |
| KR | 10-2014-0026957 A | 3/2014 |
| KR | 10-1394798 B1 | 5/2014 |
| KR | 10-1462588 B1 | 11/2014 |
| KR | 10-2014-0140177 A | 12/2014 |

* cited by examiner

FIG. 7
FIG. 8
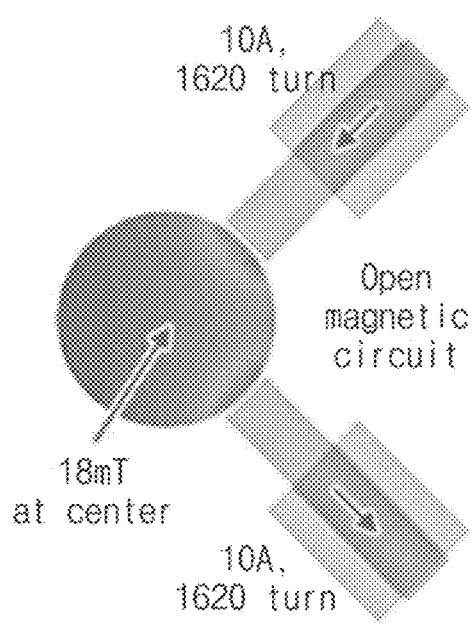
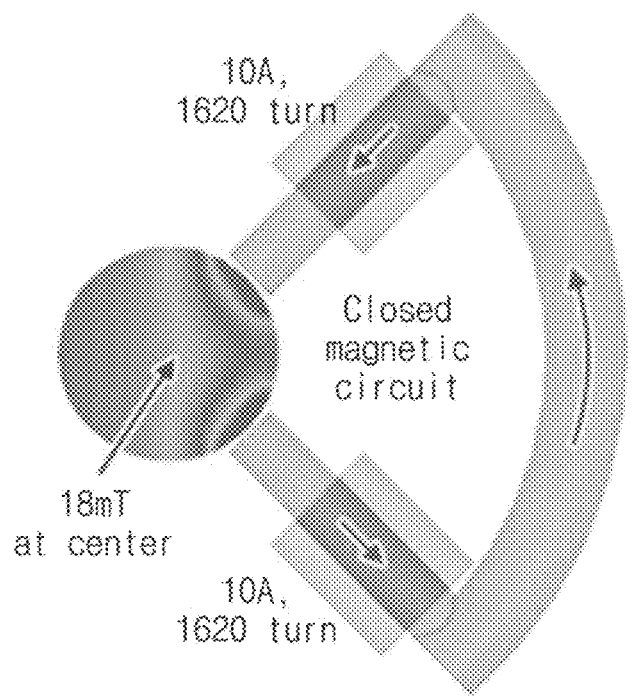

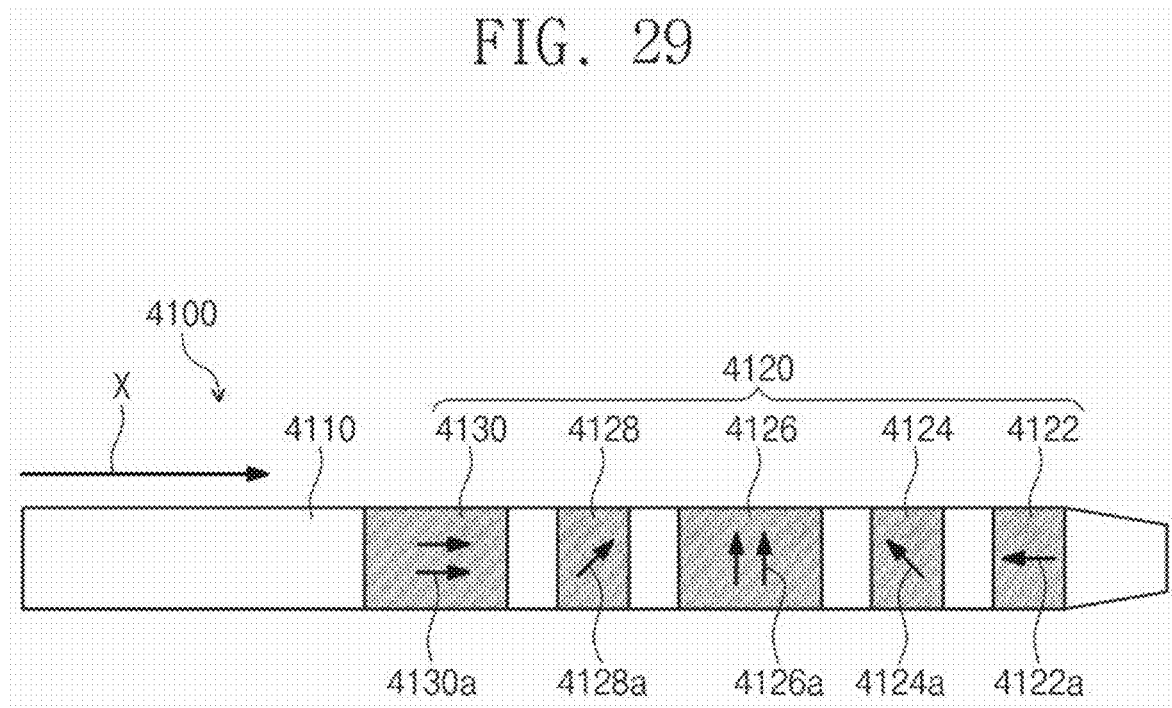

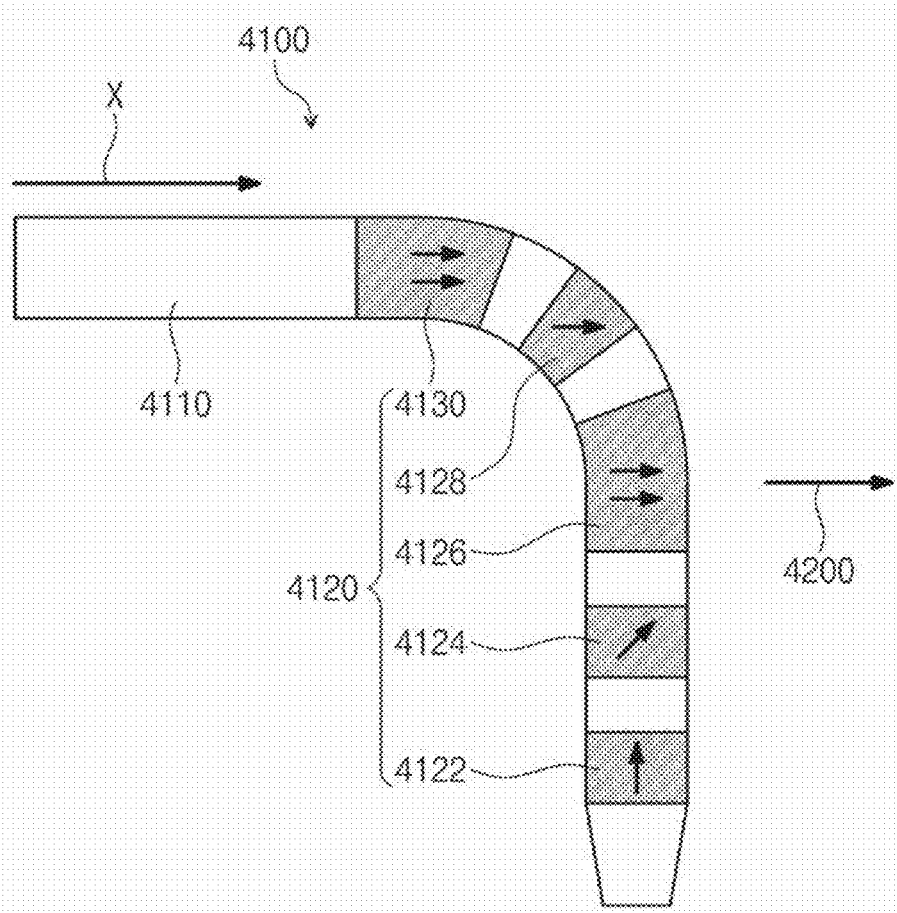

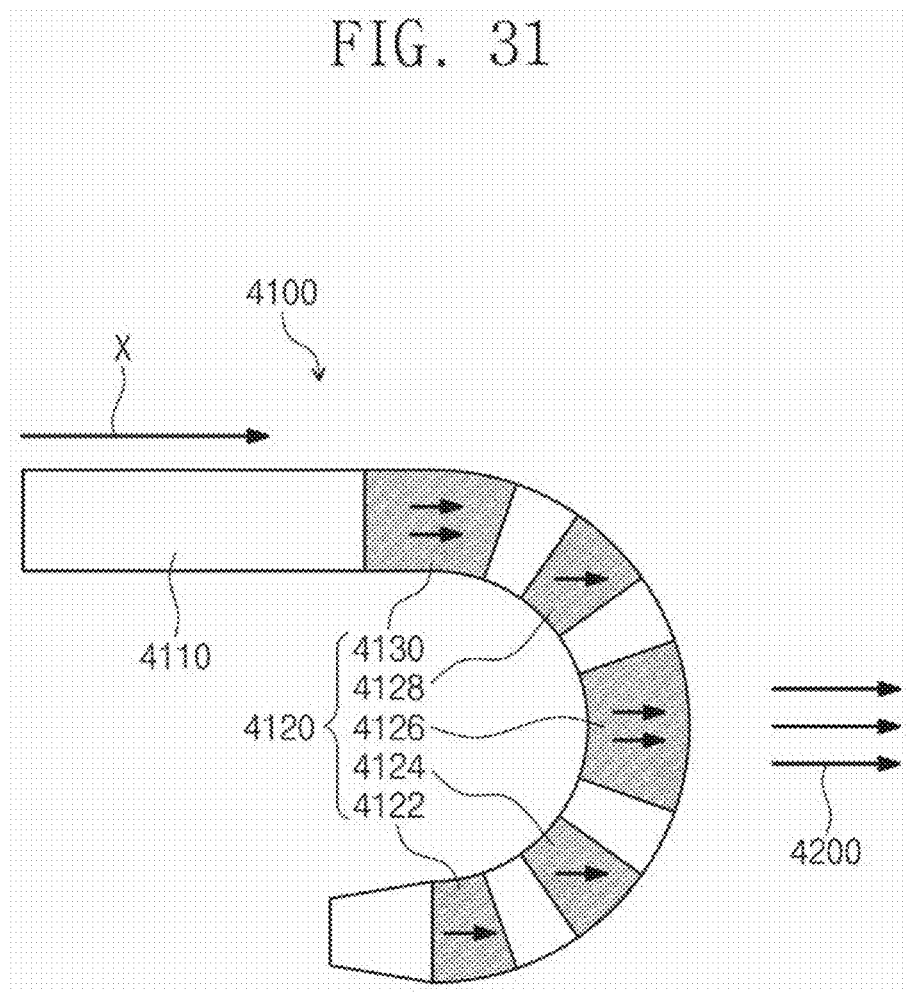

MAGNETIC FIELD CONTROL SYSTEM

TECHNICAL FIELD

The present invention relates to a magnetic field control system, and more particularly to a magnetic field control system that may control a motion of an in-pipe movement apparatus.

BACKGROUND ART

An electromagnetic driving system is a magnetic field generating apparatus for controlling a magnetic micro-robot or a magnetic catheter by using a magnetic field generated by a coil, along which currents flow. The micro-robot and the catheter have been developed as a means which is inserted into a human body to effectively perform medical actions, such as diagnosis of diseases or delivery of medicines, which may be hardly directly performed. Alternate magnetic fields are often used to drive them, and in particular, a drilling motion using a rotating magnetic field having high magnetic flux density is used to clear blood vessels that are blocked.

However, the existing electromagnetic driving system generates a magnetic field of a relatively low density by using an open magnetic circuit, and particularly the magnitude of an alternate magnetic field abruptly decreases as frequency increases due to the inductance effect. That is, according to the existing electromagnetic driving system, a magnetic field is leaked to the outside because it uses an open magnetic circuit, and the driving speed and the mission performance capacity of the micro-robot is restricted because it cannot overcome a magnetic field weakening effect due to frequency so that a high-frequency and high density magnetic field cannot be generated.

It is possible to perform a control in consideration of a magnetic field decreasing effect according to frequency by using a feedback control to overcome the restrictions, but the basic problem of low output cannot be solved. As another solution, it is possible to decrease the size of the electromagnetic driving system or increase the intensity of the magnetic field by increasing the current, but efficiency decreases due to the narrow inner space and the increased current.

DISCLOSURE

Technical Problem

Embodiments of the present invention provide a magnetic field control system that may effectively increase the intensity of a magnetic field generated in a target area.

Embodiments of the present invention also provide a magnetic field control system that may generate a magnetic field while changing a resonance frequency.

The present invention also provides a magnetic field control system that may perform a stable location control in a pipe having a pulsation environment, such as a blood vessel.

The present invention also provides a magnetic field control system that may switch directions while having a movement principle of a crawling motion.

The technical objective of the present invention is to provide a magnetic field control system having an improved steering performance.

The technical objects of the present disclosure are not limited to the above-mentioned one, and the other unmentioned technical objects will become apparent to those skilled in the art from the following description.

Technical Solution

In accordance with an aspect of the present invention, there is provided a magnetic field control system comprising: a structure forming part configured to form a three-dimensional structure having an inner space; a magnetic field generating part extending from a specific location of the structure forming part, disposed to face a target area defined in the inner space, and configured to generate a magnetic field; and a power source part configured to supply electric power to the magnetic field generating part.

The magnetic field generating unit may include a first magnetic field generating part and a second magnetic field generating part, the power source part may include a first power source part and a second power source part, the first magnetic field generating part may include: a first magnetic core extending from a specific location of the structure forming part; a first coil wound on the first magnetic core; and a first variable capacitor, one end of which is connected to an opposite end of the first coil and an opposite end of which is connected to the first power source part; and the second magnetic field generating part may include: a second magnetic core extending from a specific location of the structure forming part; a second coil wound on the second magnetic core; and a second variable capacitor, one end of which is connected to an opposite end of the second coil and an opposite end of which is connected to the second power source.

The first coil, the first variable capacitor, and the first power source part may form a first closed circuit, and a resonance frequency of the first closed circuit may vary according to a capacitance of the first variable capacitor.

The second coil, the second variable capacitor, and the second power source part may form a second closed circuit, and a resonance frequency of the second closed circuit may vary according to a capacitance of the second variable capacitor.

The capacitances of the first variable capacitor and the second variable capacitor may be set to be the same or different.

The first magnetic core and the second magnetic core may be cylindrical magnetic bodies.

Each of the first variable capacitor and the second variable capacitor may include a plurality of capacitors connected in parallel to each other.

A plurality of magnetic field generating parts may be provided, and each of the magnetic field generating parts may include: a plurality of magnetic cores extending from specific locations of the structure forming part; a plurality of coils wound on the plurality of magnetic cores, respectively; and a plurality of variable capacitors having ends of which are connected to opposite ends of the plurality of coils and opposite ends of which are connected to the power source part.

A plurality of power source parts may be provided to supply electric power to the plurality of coils, independently.

Among the plurality of coils, the plurality of variable capacitors, and the power source parts, a coil, a variable capacitor, and a power source part, which are connected to each other, may form a closed circuit, and a resonance frequency of the closed circuit may vary according to the capacitance value of the variable capacitor.

The three-dimensional structure may be a rectangular parallelepiped or a regular hexahedron, and the plurality of cores may extend from apexes of the rectangular parallelepiped or the regular hexahedron to face the target area.

The three-dimensional structure may a sphere, the structure forming part may include two circular magnetic core rings coupled to each other such that planes defined in the interior of the structure forming part are perpendicular to each other and the centers thereof coincide with each other, and the plurality of magnetic cores may be disposed to face the target area from specific locations of the two circular magnetic core rings.

Advantageous Effects

According to the present invention, the intensity of a magnetic field generated in a target area may be effectively increased.

Further, according to the present invention, a magnetic field may be generated while a resonance frequency is changed.

Further, according to the present invention, a moving robot is compulsorily synchronized with a magnetic field by generating an external magnetic field that vibrates while rotating, and a specific motion performance may be always maintained regardless of a posture and a stable position may be maintained by making a crawling motion by using frictional forces between the legs of the moving robot and a wall of a pipe.

Further, according to the present invention, the direction of the moving robot, including a forward movement and a backward movement, may be switched regardless of the diameter of the pipe.

Further, according to the present invention, the steering performance of the tube may be improved by providing two or more magnetic bodies, of which the directions or magnitudes of the magnetic moments are different

DESCRIPTION OF THE DRAWINGS

FIG. 7 is a view illustrating a magnetic field generated by a general magnetic field generating apparatus;

FIG. 8 is a view illustrating a magnetic field generated by the magnetic field generating apparatus according to the first embodiment of the present invention;

FIG. 29 is a view illustrating a magnetic tube system according to a fifth embodiment of the present invention;

FIG. 30 is a view illustrating a modification of the magnetic tube system according to the fifth embodiment of the present invention when an external magnetic field of a low intensity is applied to the magnetic tube system; and FIG. 31 is a view illustrating a modification of the magnetic tube system according to the fifth embodiment of the present invention when an external magnetic field of a high intensity is applied to the magnetic tube system.

BEST MODE

Figure 1:
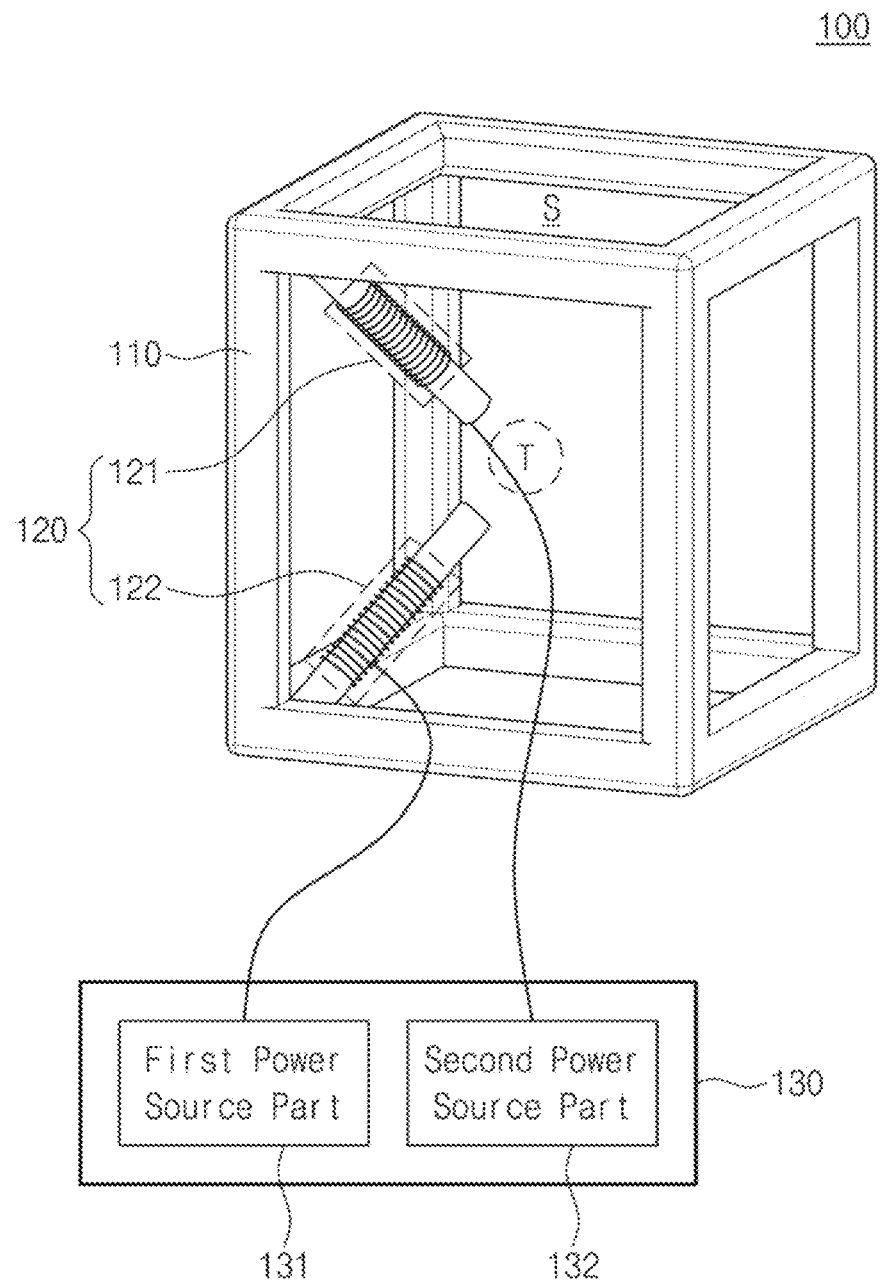
FIG. 1 illustrates a magnetic field generating apparatus according to a first embodiment of the present invention.

A magnetic field control apparatus according to an embodiment of the present invention may include a structure forming part configured to form a three-dimensional structure having an inner space, a magnetic field generating part extending from a specific location of the structure forming part, disposed to face a target area defined in the inner space, and configured to generate a magnetic field, and a power source part configured to supply electric power to the magnetic field generating part.

MODE

Hereinafter, exemplary embodiments of the present disclosure will be described in detail with reference to the accompanying drawings. Throughout the specification, it is noted that the same or like reference numerals denote the same or like components even though they are provided in different drawings. Further, in the following description of the present disclosure, a detailed description of known functions and configurations incorporated herein will be omitted when it may make the subject matter of the present disclosure rather unclear.

In addition, terms, such as first, second, A, B, (a), (b) or the like may be used herein when describing components of the present disclosure. The terms are provided only to distinguish the components from other components, and the essences, sequences, orders, and numbers of the components are not limited by the terms. In addition, unless defined otherwise, all terms used herein, including technical or scientific terms, have the same meanings as those generally understood by those skilled in the art to which the present disclosure pertains. The terms defined in the generally used dictionaries should be construed as having the meanings that coincide with the meanings of the contexts of the related technologies, and should not be construed as ideal or excessively formal meanings unless clearly defined in the specification of the present disclosure.

A magnetic field control system according to the present invention includes a magnetic field generating apparatus and an in-pipe movement apparatus. The magnetic field generating apparatus generates an external magnetic field outside a pipe and remotely controls an in-pipe movement apparatus. The in-pipe movement apparatus may move in various pipe environments, such as tubular tissues of human bodies including blood vessels, digestive organs, and urethras, domestic pipes, and industrial pipes, and may check and diagnose the environments in pipes. The in-pipe movement apparatus includes a moving robot and a magnetic tube system.

Although an example of using a magnetic control system for pipe environments in human bodies will be mainly described in the present invention, the technical items of the present invention are not limited thereto and may be variously changed.

Figure 2:
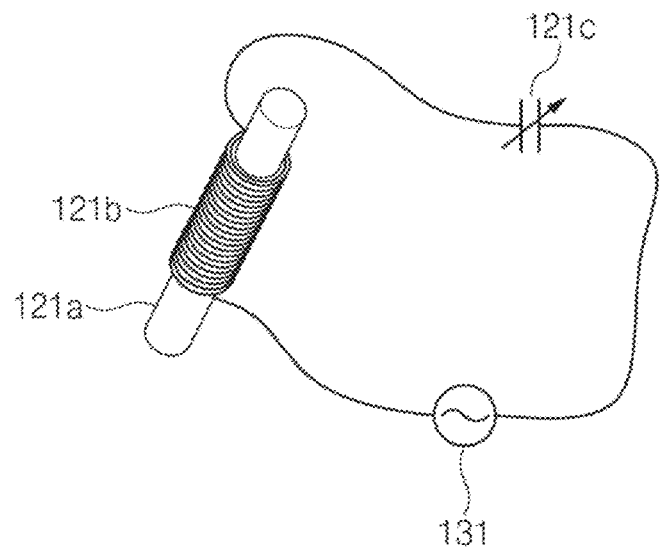
FIG. 2 illustrates a first magnetic field generating part of the magnetic field generating apparatus according to the first embodiment of the present invention in detail.
Figure 3:
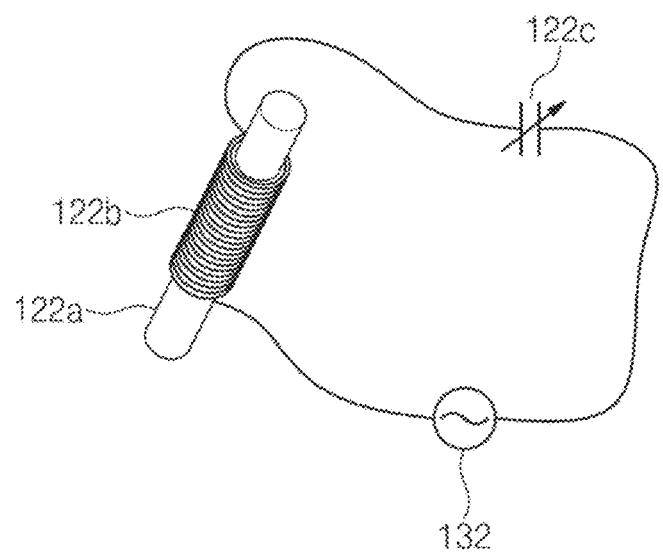
FIG. 3 illustrates a second magnetic field generating part of the magnetic field generating apparatus according to the first embodiment of the present invention in detail.

FIG. 1 illustrates a magnetic field generating apparatus according to a first embodiment of the present invention. FIG. 2 illustrates a first magnetic field generating part of the magnetic field generating apparatus according to the first embodiment of the present invention in detail. FIG. 3 illustrates a second magnetic field generating part of the magnetic field generating apparatus according to the first embodiment of the present invention in detail.

First, referring to FIG. 1, the magnetic field generating apparatus 100 according to the first embodiment of the present invention may include a structure forming part 110, a magnetic field generating part 120, and a power source part 130.

The structure forming part 110 may form various three-dimensional structures having an inner space S. For example, the three-dimensional structure may include a three-dimensional figure having various forms, such as a regular hexahedron, a rectangular parallelepiped, a sphere, and a cylinder. Accordingly, although it is illustrated in FIG. 1 that the structure forming part 110 forms a three-dimensional structure of a regular hexahedron or a rectangular parallelepiped, the present invention is not limited thereto. A target area T may be defined in a specific area of the inner space S. For example, the target area T may mean an area in which a magnetic field is generated. The structure forming part 110 is formed of a magnetic body of a high magnetic permeability, and may perform a function of amplifying an intensity of a magnetic field.

The magnetic field generating part 120 may extend from a specific location (for example, an apex) of the structure forming part (110), and may be disposed to face the target area T defined by the inner space S. Through the structure forming part 110 and the magnetic field generating part 120, which have been described above, the magnetic field generating part 120 may generate a magnetic field of a high density in the target area T by reducing leakage of a magnetic field to the outside. The magnetic field generating part 120 may include a first magnetic field generating part 121 and a second magnetic field generating part 122.

Referring to FIG. 1, the first magnetic field generating part 121 may include a first magnetic core 121a extending from a specific location of the structure forming part 110, a first coil 121b wound on the first magnetic core 121a and one end of which is connected to a first power source part 131, and a first variable capacitor 121c, one end of which is connected to an opposite end of the first coil 121b and an opposite end of which is connected to the first power source part 131. For example, the first magnetic core 121a may be formed of a cylindrical magnetic body. For example, the first variable capacitor 121c may include a plurality of capacitors that are connected to each other in parallel.

The first coil 121b, the first variable capacitor 121c, and the first power source part 131 may form a first closed circuit. For example, the first coil 121b may include components of a resistor R and an inductor L, and accordingly, a resonance frequency of the first closed circuit including the resistor R, the inductor L, and the first variable capacitor 121c may vary according to a capacitance of the first variable capacitor 121c.

Referring to FIG. 3, the second magnetic field generating part 122 may include a second magnetic core 122a extending from a specific location of the structure forming part 110, a second coil 122b wound on the second magnetic core 122a and one end of which is connected to a second power source part 132, and a second variable capacitor 122c, one end of which is connected to an opposite end of the second coil 122b and an opposite end of which is connected to the second power source part 132. For example, the second magnetic core 122a may be formed of a cylindrical magnetic body. For example, the second variable capacitor 122c may include a plurality of capacitors that are connected to each other in parallel.

The second coil 122b, the second variable capacitor 122c, and the second power source part 132 may form a second closed circuit. For example, the second coil 122b may include components of a resistor R and an inductor L, and accordingly, a resonance frequency of the second closed circuit including the resistor R, the inductor L, and the second variable capacitor 122c may vary according to a capacitance of the second variable capacitor 122c.

That is, because capacitances due to the variable capacitors (that is, the first variable capacitor 121c and the second variable capacitor 122c) may be added to the inductances in the first closed circuit and the second closed circuit, which have been described above, a resonance, by which a magnetic field is maximized at a specific frequency, may be generated. Then, a resonant point may be adjusted through control of the capacitances of the first variable capacitor 121c and the second variable capacitor 122c, a resonance may be generated at any frequency as long as a change range of the capacitances is sufficient. For example, the capacitances of the first variable capacitor 121c and the second variable capacitor 122c may be set to be the same or different.

Accordingly, a magnetic field may be generated at a specific frequency (for example, a frequency of an input voltage) by adjusting the capacitance of the first variable capacitor 121c and/or the second variable capacitor 122c such that a resonance may be generated at a desired frequency.

Then, currents flowing through the first coil 121b and the second coil 122b may be expressed as in Equation 1.

$$I = \frac{V_s}{\sqrt{R_c^2 + \left(2\pi f L_c - \frac{1}{2\pi f C_v}\right)^2}}$$ [Equation 1]

Here, $V_s$ is an intensity of an applied voltage, f is a frequency of the applied voltage, $R_c$ and $L_c$ are a resistance and an inductance of a coil, and $C_v$ is a capacitance of a variable capacitor. The maximum voltage is obtained at a resonance frequency of the closed circuit of $f_c(=\sqrt{1/4\pi^2 C_v L_c})$, and the resonance frequency may be adjusted by the variable capacitor.

Referring back to FIG. 1, the power source part 130 may supply electric power to the magnetic field generating part 120. The power source part 130 may include a first power source part 131 configured to supply electric power to the first magnetic field generating part 121 and a second power source part 132 configured to supply electric power to the second magnetic field generating part 122. Although it has been described in FIG. 1 that the first power source part 131 and the second power source part 132 are distinguished, the power source part 130 may be configured to independently supply electric power to the first magnetic field generating part 121 and the second magnetic field generating part 122.

Figure 4:
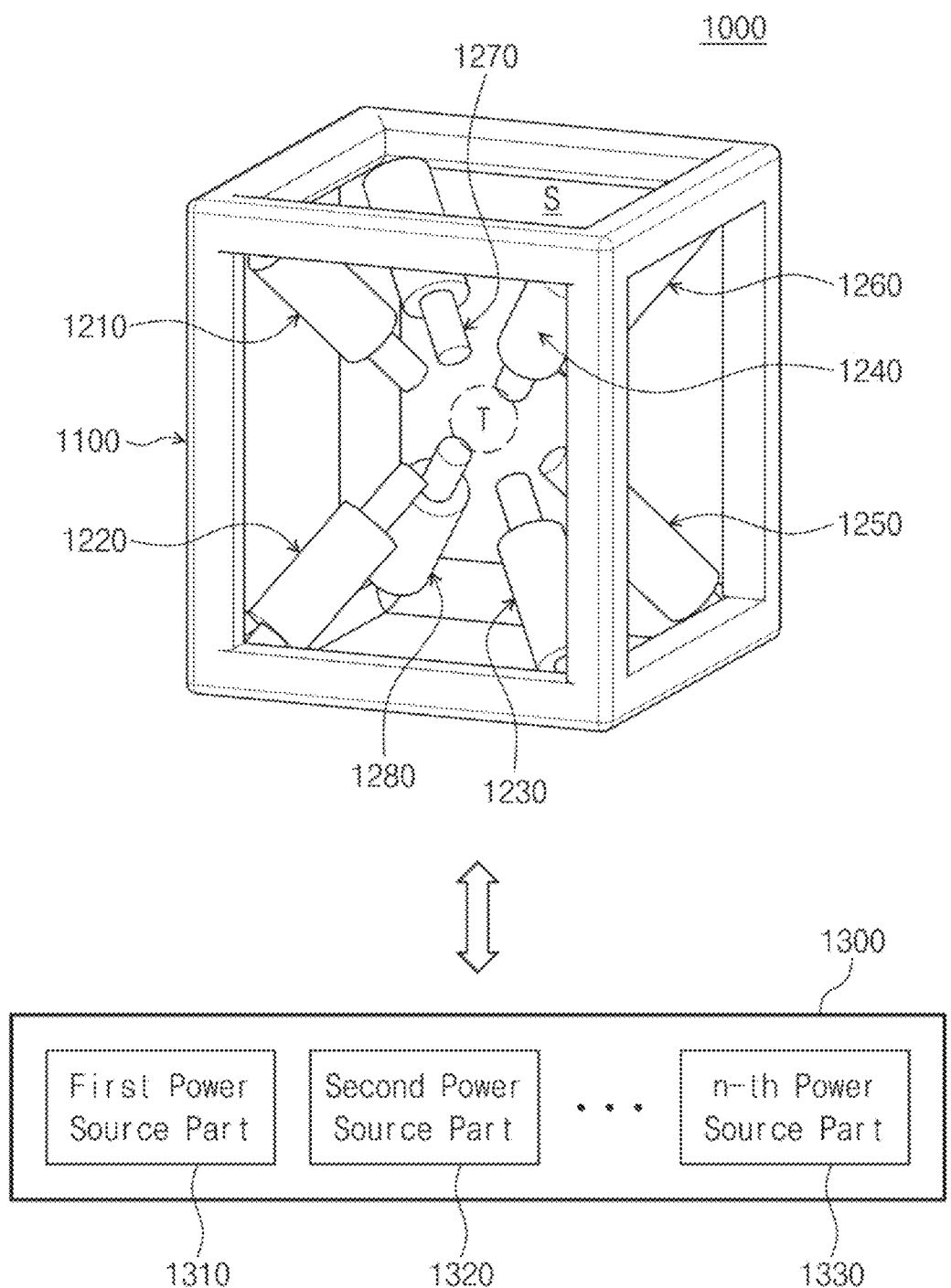
FIG. 4 illustrates a magnetic field generating apparatus according to a second embodiment of the present invention.
Figure 5:
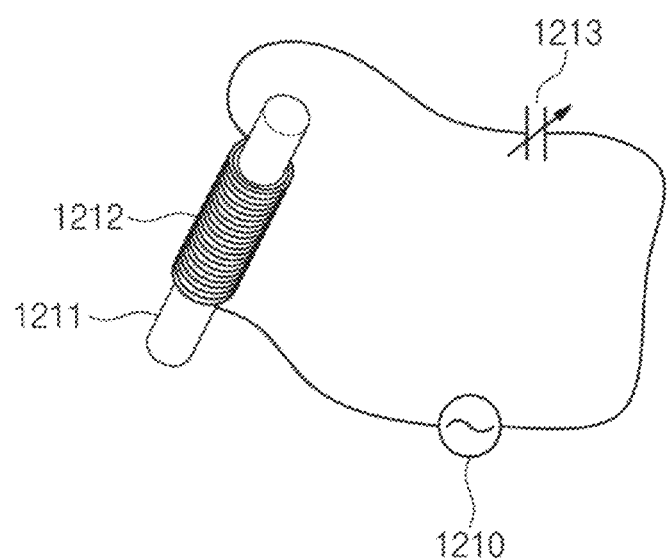
FIG. 5 illustrates one of a plurality of magnetic field generating parts of the magnetic field generating apparatus according to the second embodiment of the present invention in detail.

FIG. 4 illustrates a magnetic field generating apparatus according to a second embodiment of the present invention. FIG. 5 illustrates one of a plurality of magnetic field generating parts of the magnetic field generating apparatus according to the second embodiment of the present invention in detail.

First, referring to FIG. 4, the magnetic field generating apparatus 100 according to the second embodiment may have a three-dimensional structure of a regular hexahedron or a rectangular parallelepiped.

The magnetic field generating apparatus 1000 according to the second embodiment of the present invention may include a structure forming part 1100, magnetic field generating parts 1210 to 1280, and a power source part 1300.

The structure forming part 1100 may form a structure of a regular hexahedron or rectangular parallelepiped having an inner space S. A target area T may be defined in a specific area of the inner space S. For example, the target area T may mean an area in which a magnetic field is generated. The structure forming part 1100 is formed of a magnetic body of a high magnetic permeability, and may perform a function of amplifying an intensity of a magnetic field.

The magnetic field generating parts 1210 to 1280 may extend from specific locations (for example, eight apexes) of the structure forming part (1100), and may be disposed to face the target area T defined by the inner space S. Through the structure forming part 1100 and the magnetic field generating parts 1210 to 1280, which have been described above, the magnetic field generating parts 1210 to 1280 may generate magnetic fields of high density in the target area T by reducing leakage of magnetic fields to the outside. A plurality of magnetic field generating parts 1210 to 1280 may be provided, and although eight magnetic field generating parts 1210 to 1280 are illustrated in FIG. 4, the present invention is not limited thereto.

Referring to FIG. 5, the magnetic field generating part 1210 is illustrated. The magnetic field generating part 1210 may include a magnetic core 1211 extending from a specific location (for example, any one of the eight apexes) of the structure forming part 1100, a coil 1212 wound on the magnetic core 1211 and one of which is connected to the first power source part 1310, and a variable capacitor 1213, one end of which is connected to an opposite end of the coil 1212 and an opposite end of which is connected to the first power source part 1310. For example, the magnetic core 1211 may be formed of a cylindrical magnetic body. For example, the first variable capacitor 1213 may include a plurality of capacitors that are connected to each other in parallel.

The coil 1212, the variable capacitor 1213, and the first power source part 1310 may form a closed circuit. For example, the coil 1212 may include components of a resistor R and an inductor L, and accordingly, a resonance frequency of the second closed circuit including the resistor R, the inductor L, and the variable capacitor 1213 may vary according to a capacitance of the variable capacitor 1213.

Meanwhile, the description related to FIG. 5 may be applied the other magnetic field generating parts 1220 to 1280 in the same way. For example, each of the magnetic field generating parts 1220 to 1280 may include a magnetic core, a coil, and a variable capacitor, and each of the magnetic field generating parts 1220 to 1280 may receive electric power from the corresponding power source part 1320 to 1330 and the coil, the variable capacitor, and the power source part thereof may form a closed circuit.

That is, because a capacitance due to the variable capacitor may be added to the closed circuit formed by each of the plurality of magnetic field generating parts 1210 to 1280 in addition to the inductance, a resonance at which a magnetic field is maximized at a specific frequency may be generated. Then, the resonant point may be adjusted through control of the capacitance of each of the variable capacitors, a resonance may be generated at any frequency as long as a range of a change of the capacitance is sufficient. For example, the capacitances of the variable capacitors may be set to be the same or different.

Figure 6:
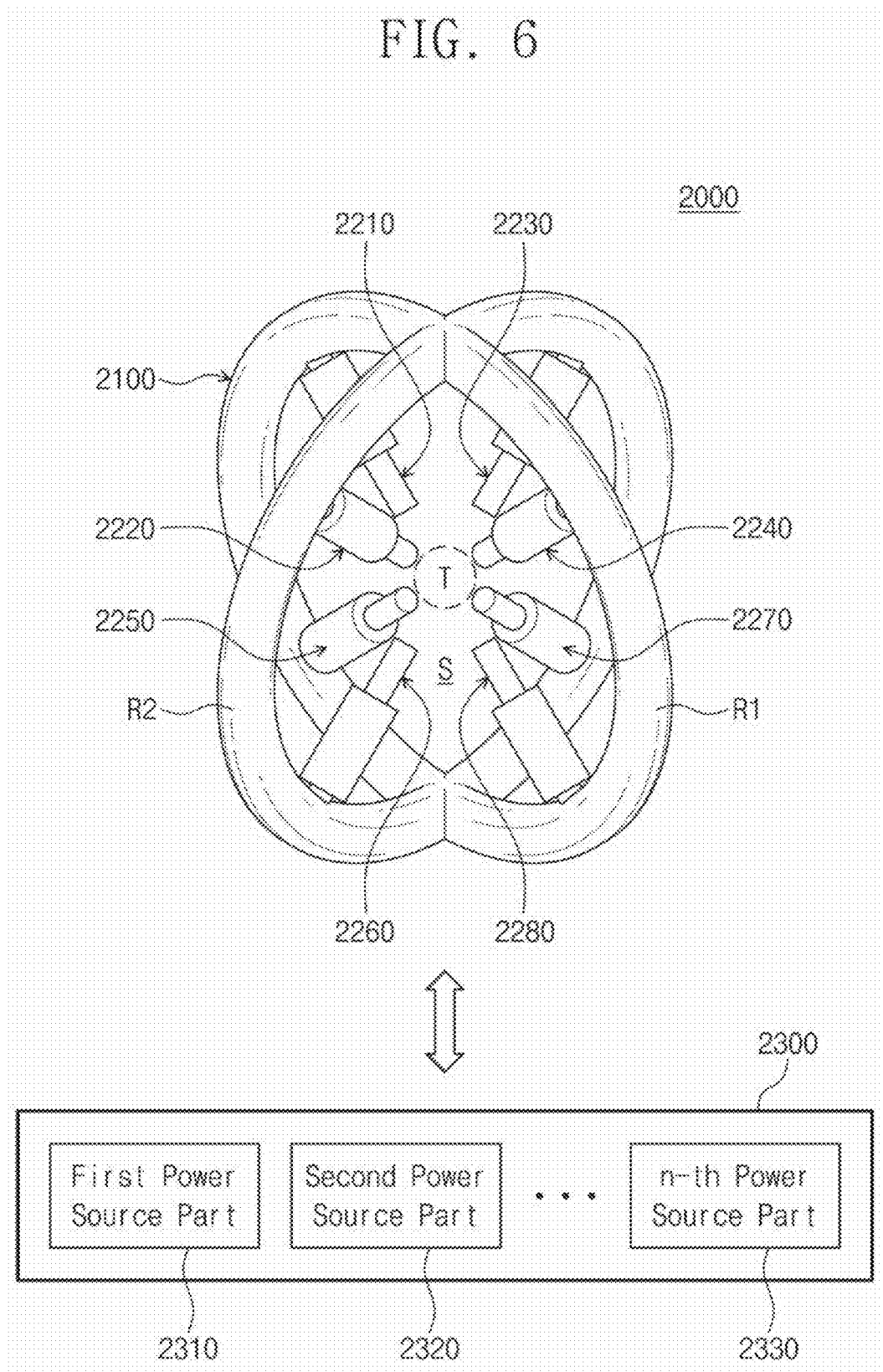
FIG. 6 illustrates a magnetic field generating apparatus according to a third embodiment of the present invention.

Accordingly, a magnetic field may be generated at a specific frequency (for example, a frequency of an input voltage) by adjusting the capacitances of the variable capacitors such that a resonance is generated at a desired frequency FIG. 6 illustrates a magnetic field generating apparatus according to a third embodiment of the present invention.

Referring to FIG. 6, the magnetic field generating apparatus 2000 according to the third embodiment of the present invention may have a three-dimensional structure of a form of a sphere.

The magnetic field generating apparatus 2000 according to the third embodiment of the present invention may include a structure forming part 2100, magnetic field generating parts 2210 to 2280, and a power source part 2300.

The magnetic field generating apparatus 2000 according to the third embodiment of the present invention, which is illustrated in FIG. 6, may be substantially the same as the magnetic field generating apparatus 1000 according to the second embodiment of the present invention, which has been described with reference to FIGS. 4 and 5, in the aspects of the operations and functions of the magnetic field generating part 2210 to 2280, except for the aspect of the structures and disposals of the structure forming part 2100 and the magnetic field generating parts 2210 to 2280. Accordingly, the differences will be mainly described briefly to avoid repetition of unnecessary descriptions.

The structure forming part 2100 may form a structure of a sphere having an inner space S. A target area T may be defined in a specific area of the inner space S. The structure forming part 2100 may include two circular magnetic core rings R1 and R2, which are coupled to each other such that defined planes thereof are perpendicular to each other and the center points thereof coincide with each other, in the interior thereof.

The magnetic field generating parts 2210 to 2280 may extend from specific locations (for example, specific locations of the circular magnetic core rings R1 and R2) of the structure forming part (2100), and may be disposed to face the target area T defined by the inner space S. Through the structure forming part 2100 and the magnetic field generating parts 2210 to 2280, which have been described above, the magnetic field generating parts 2210 to 2280 may generate magnetic fields of high density in the target area T by reducing leakage of magnetic fields to the outside. A plurality of magnetic field generating parts 2210 to 2280 may be provided, and although eight magnetic field generating parts 2210 to 2280 are illustrated in FIG. 6, the present invention is not limited thereto.

The detailed structures of the magnetic field generating parts 2210 to 2280 may be the same as described above with reference to FIG. 5. Accordingly, a magnetic field may be generated at a specific frequency (for example, a frequency of an input voltage) by adjusting the capacitances of the variable capacitors such that a resonance is generated at a desired frequency FIG. 7 is a view illustrating a magnetic field generated by a general magnetic field generating apparatus; FIG. 8 is a view illustrating a magnetic field generated by the magnetic field generating apparatus according to the first embodiment of the present invention.

Referring to FIGS. 7 and 8, when currents of 10A are applied to the first magnetic core 121a of a diameter of 70 mm and a length of 250 mm, on which the first coil 121b is wound 1620 times and the second magnetic core 122a of a diameter of 70 mm and a length of 250 mm, on which the second coil 121b is wound 1620 times, magnetic fields at a location (that is, the target area T) that is spaced apart from ends of the first magnetic core 121a and the second magnetic core 122a by 125 mm is calculated to be 18 mT and 58 mT in an open magnetic circuit (see FIG. 7) and a closed magnetic circuit (that is, the magnetic field generating apparatus 100 according to the first embodiment of the present invention, see FIG. 8). This means that the magnetic field generating capacity of the magnetic field generating apparatus 100 according to the first embodiment of the present invention is not less than three times as compared with the case in which a general magnetic field generating apparatus is used.

Figure 9:
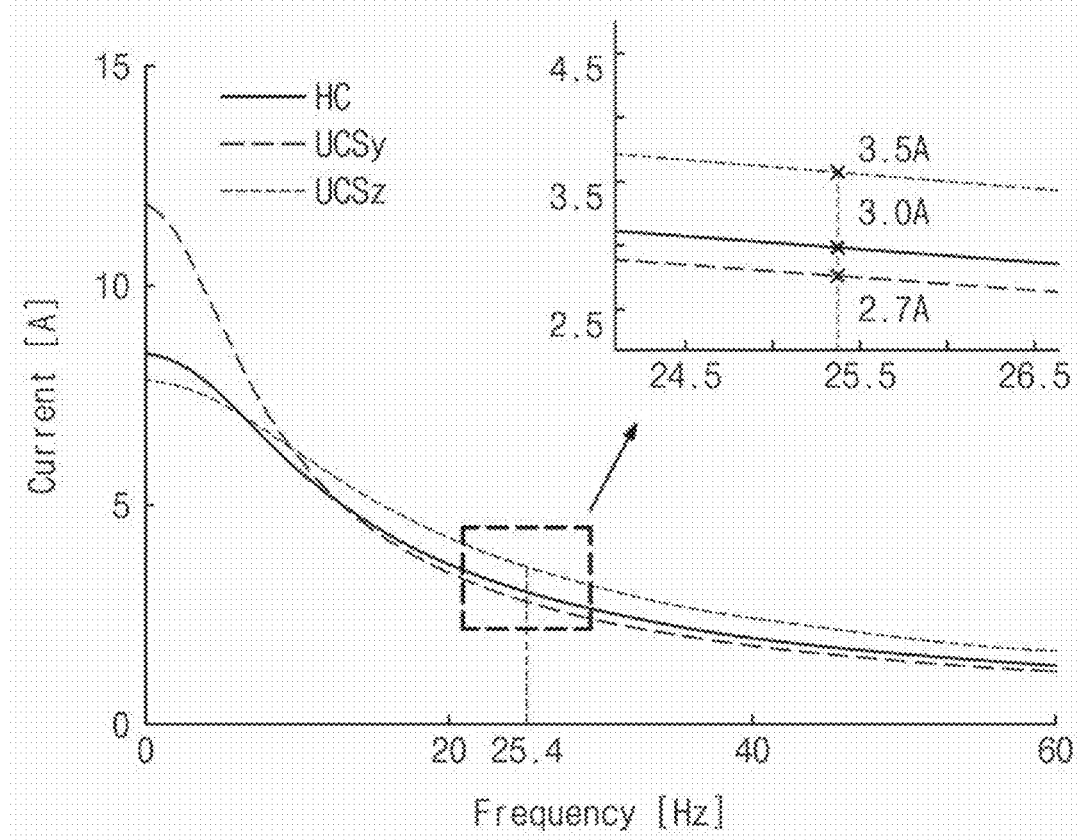
FIG. 9 is a view illustrating a change of a magnetic field according to a change of a frequency of a voltage applied to a magnetic field generating apparatus having no variable capacitor.
Figure 10:
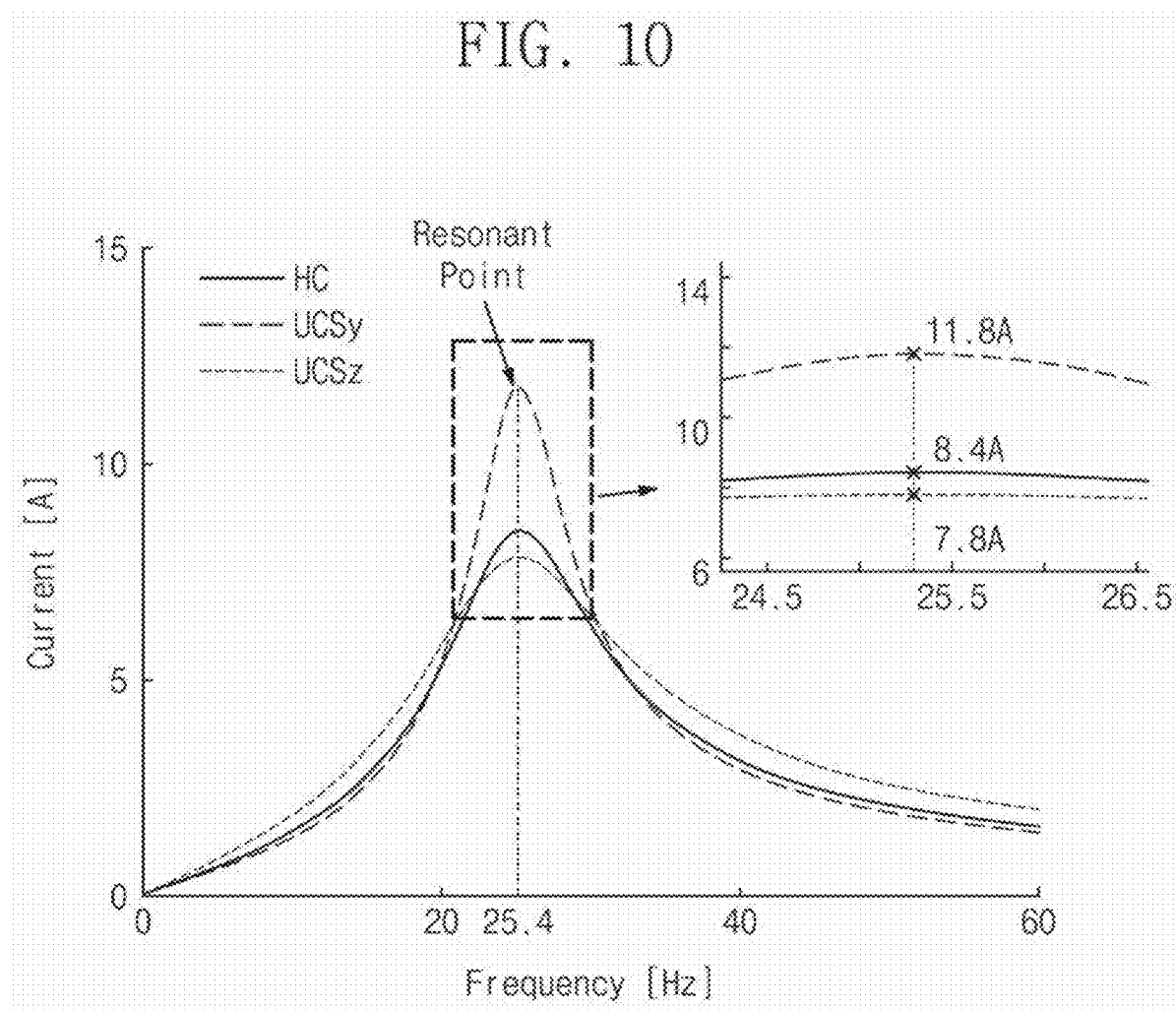
FIG. 10 is a view illustrating a change of a magnetic field according to a change of a frequency of a voltage applied to a magnetic field generating apparatus having a variable capacitor.

FIG. 9 is a view illustrating a change of a magnetic field according to a change of a frequency of a voltage applied to a magnetic field generating apparatus having no variable capacitor. FIG. 10 is a view illustrating a change of a magnetic field according to a change of a frequency of a voltage applied to a magnetic field generating apparatus having a variable capacitor.

Referring to FIG. 9, it is identified that the generated current decreases as the frequency of the voltage applied increases due to an inductance effect. On the other hand, referring to FIG. 10, it is identified that the capacitance of the variable capacitor is adjusted to generate a resonance at a frequency of 25.4 Hz and the current generated increases by about 2.2 to 4.3 times as compared with the case in which there is no variable capacitor. It may be identified that the intensity of the rotating magnetic field that may be generated at a frequency of 25.4 Hz when there is no variable capacitor is 5 mT due to a current increase effect whereas the current increases to 14 mT when there is a variable capacitor.

Figure 11:
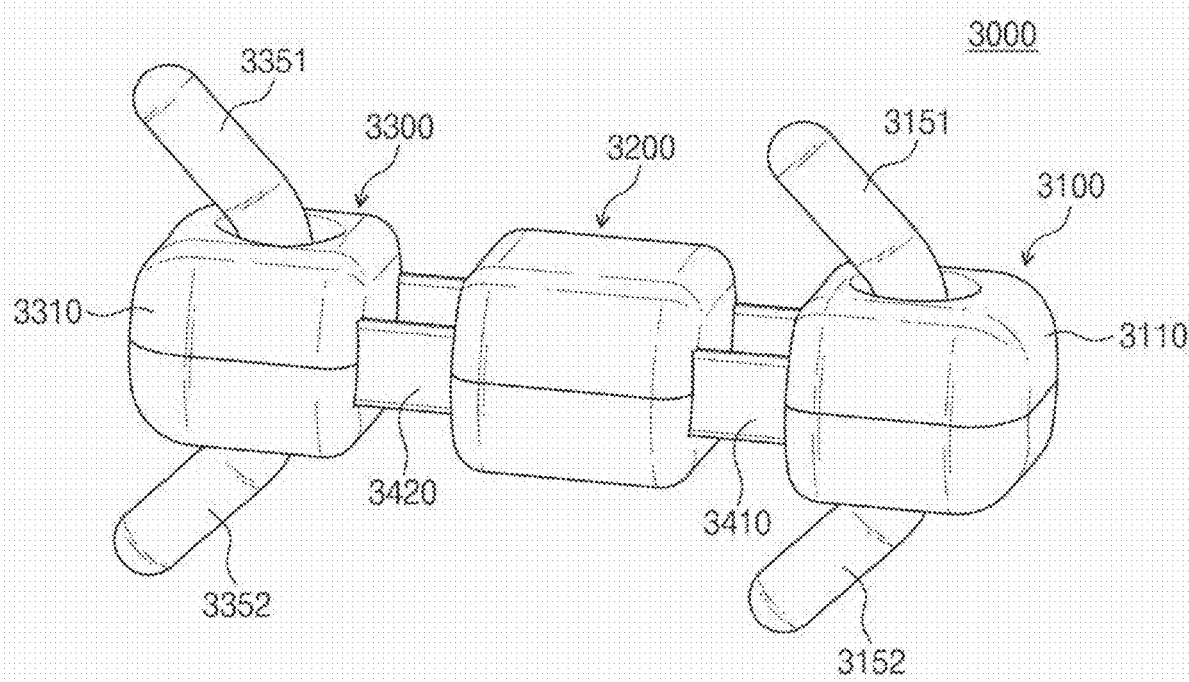
FIG. 11 is a perspective view illustrating a moving robot according to an embodiment of the present invention.
Figure 12:
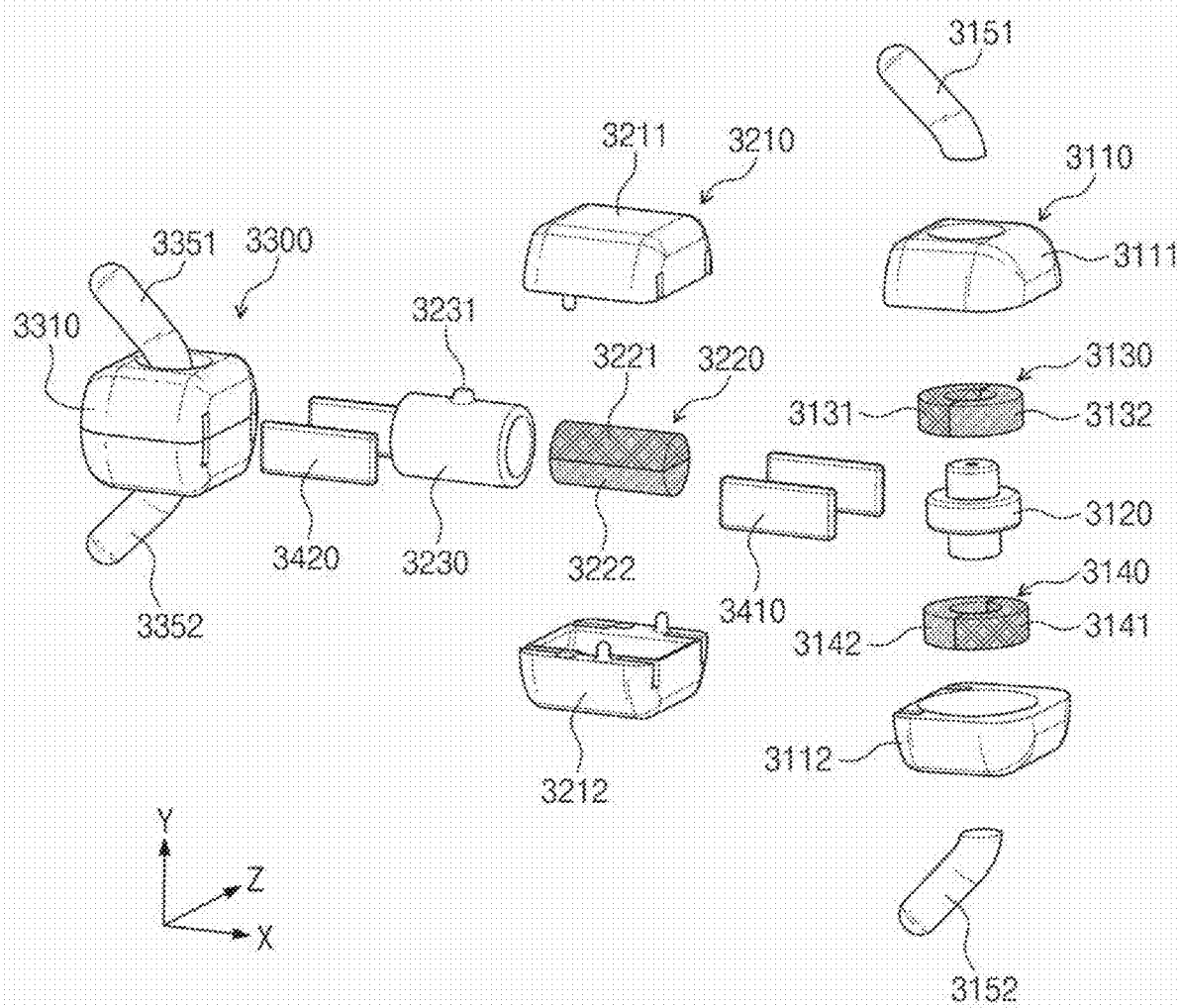
FIG. 12 is an exploded perspective view of the moving robot of FIG. 11.

FIG. 11 is a perspective view illustrating a moving robot according to an embodiment of the present invention. FIG. 12 is an exploded perspective view of the moving robot of FIG. 11.

Referring to FIGS. 11 and 12, the moving robot 3000 moves as a crawling motion is formed by compulsorily synchronizing magnetic fields of the magnets with an external magnetic field that vibrates while rotating.

The moving robot 3000 includes a first steering module 3100, a movement module 3200, a second steering module 3300, and first and second connecting parts 3410 and 3420.

The first steering module 3100, the movement module 3200, and the second steering module 3300 may be sequentially located. The first steering module 3100 and the second steering module 3300 switch a direction of the moving robot 3000, and generate a motion of the robot due to the crawling motion. The movement module 3200 is controlled by the above-described external magnetic field, and provides driving forces to the first steering module 3100 and the second steering module 3300 by using a magnetic force. Further, the first connecting part 3410 connects the first steering module 3100 and the movement module 3200, and the second connecting part 3420 connects the movement module 3200 and the second steering module 3300. According to an embodiment, a pair of thin plates are provided to each of the first connecting part 3410 and the second connecting part 3420 and are arranged in parallel to connect the first steering module 3100, the movement module 3200, and the second steering module 3300.

The first steering module 3100 includes a first steering body 3110, a first spacer 3120, a first steering magnet 3130, a second steering magnet 3140, and a pair of legs 3151 and 3152.

The first steering body 3110 has a space for accommodating configurations 3120, 3130, and 3140 of the first steering module 3100, in the interior thereof. According to an embodiment, the first steering body 3110 may be configured such that an upper part 3111 and a lower part 3112 may be separated from each other.

The first spacer 3120 is provided in the first steering body 3110, and is provided to be rotatable about a first direction Y. According to an embodiment, the first spacer 3120 may be configured such that an upper end and a lower end thereof have cylindrical shapes, respectively.

The first steering magnet 3130 is inserted into and fixed to an upper end of the first spacer 3120, and the second steering magnet 3140 is inserted into and fixed to a lower end of the first spacer 3120. Each of the first steering magnet 3130 and the second steering magnet 3140 has a ring shape having an inner diameter corresponding to the upper end and the lower end of the first spacer 3120. The first steering magnet 3130 and the second steering magnet 3140 are rotated integrally with the first spacer 3120.

The first steering magnet 3130 and the second steering magnet 3140 are magnetized transversely. According to an embodiment, the N poles 3131 and 3141 and the S poles 3132 and 3142 of the first steering magnet 3130 and the second steering magnet 3140 are arranged transversely.

The first steering magnet 3130 and the second steering magnet 3140 are located in the first spacer 3120 to be spaced apart from each other by a specific distance, and are disposed such that the opposite polarities thereof face each other. In detail, the N pole 3131 of the first steering magnet 3130 and the S pole 3142 of the second steering magnet 3140 are disposed in the first direction to face each other, and the S pole 3132 of the first steering magnet 3130 and the N pole 3141 of the second steering magnet 3140 are disposed to face each other. Accordingly, the total sum of the magnetic moments between the first steering magnet 3130 and the second steering magnet 3140 becomes zero. Due to this, the force or torque by the external magnetic field does not influence the motions of the first steering magnet 3130 and the second steering magnet 3140.

The pair of legs 3151 and 3152 are rods of a specific length, and are coupled to the upper end and the lower end of the first spacer 3120, respectively. The legs 3151 and 3152 are rotated integrally with the first spacer 3120. According to an embodiment, the legs 3151 and 3152 are connected to the first spacer 3120 at a specific inclination with respect to the first direction Y, and ends of the legs 3152 and 3152 are rounded.

Figure 13:
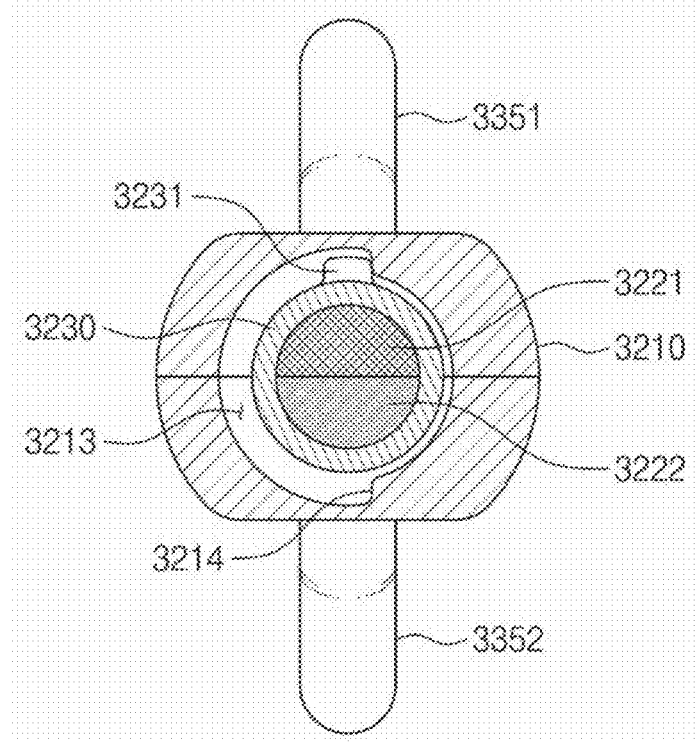
FIG. 13 is a sectional view illustrating a movement module of FIG. 11.

FIG. 13 is a sectional view illustrating a movement module of FIG. 11.

Referring to FIGS. 11 to 13, the movement module 3200 includes a movable body 3210, a movable magnet 3220, and a movable magnet cover 3230.

The movable body 3210 has a space for accommodating the movable magnet 3220 and the movable magnet cover 3230, in the interior thereof. The movable body 3210 may be configured such that an upper part 3211 and a lower part 3212 thereof may be separated from each other. A guide groove 3213 and a stopping step 3214 are formed in the inner space of the movable body 3210. According to an embodiment, the guide groove 3213 is formed within a range of 0° to 180° along an inner circumference of the movable body 3210, and the stopping step 3214 is formed within a range of 180° to 360°.

The movable magnet 3220 is located in the interior of the movable body 3210, and is configured such that the length thereof extends long in the second direction X that is perpendicular to the first direction Y. According to an embodiment, the movable magnet 3220 has a cylindrical shape and has a central axis of the second direction X. The movable magnet 3220 is magnetized in a direction that is perpendicular to the second direction X. A half of a section of the movable magnet 3220 that is perpendicular to the second direction is provided as the N pole 3221, and the remaining half is provided as the S pole 3222. The movable magnet 3220 may be rotated about the second direction X by a force and a torque of an external magnetic field.

The movable magnet cover 3230 has a cylindrical shape, a front surface and a rear surface of which are opened, and has a space for accommodating the movable magnet 3220, in the interior thereof. The movable magnet cover 3230 surrounds an outer peripheral surface of the movable magnet 3220. A stopping boss 3231 is formed on an outer surface of the movable magnet cover 3230. The stopping boss 3231 is located in the guide groove 3213, and is moved in the guide groove 3213 as the movable magnet 3220 rotates. The stopping boss 3231 may move within a range of 0° to 180° along the guide groove 3213. Further, the movement of the stopping boss 3231 is restricted to a range of 180° to 360° by the stopping step 3214.

The second steering module 3300 includes a second steering body 3310, a second spacer (not illustrated), a third steering magnet 3351, a fourth steering magnet (not illustrated), and a pair of legs 3151 and 3152. Because the configurations of the second steering module 3300 have the same structures as the configurations of the first steering module 3100, a detailed description thereof will be omitted.

Hereinafter, a driving principle of the above-described moving robot will be described in detail.

The moving robot 3100 moves due to a magnetic torque motion of the movable magnet 3220 by an external magnetic field, as in Equation 1.

$$\vec{T} = \vec{M}_a \times \vec{B} \quad \text{[Equation 1]}$$

Here, $\vec{T}$ is a magnetic torque generated by an external magnetic field, $\vec{M}_a$ is a magnetic moment of the movable magnet, and $\vec{B}$ is a magnetic flux of the external magnetic field.

Figure 14:
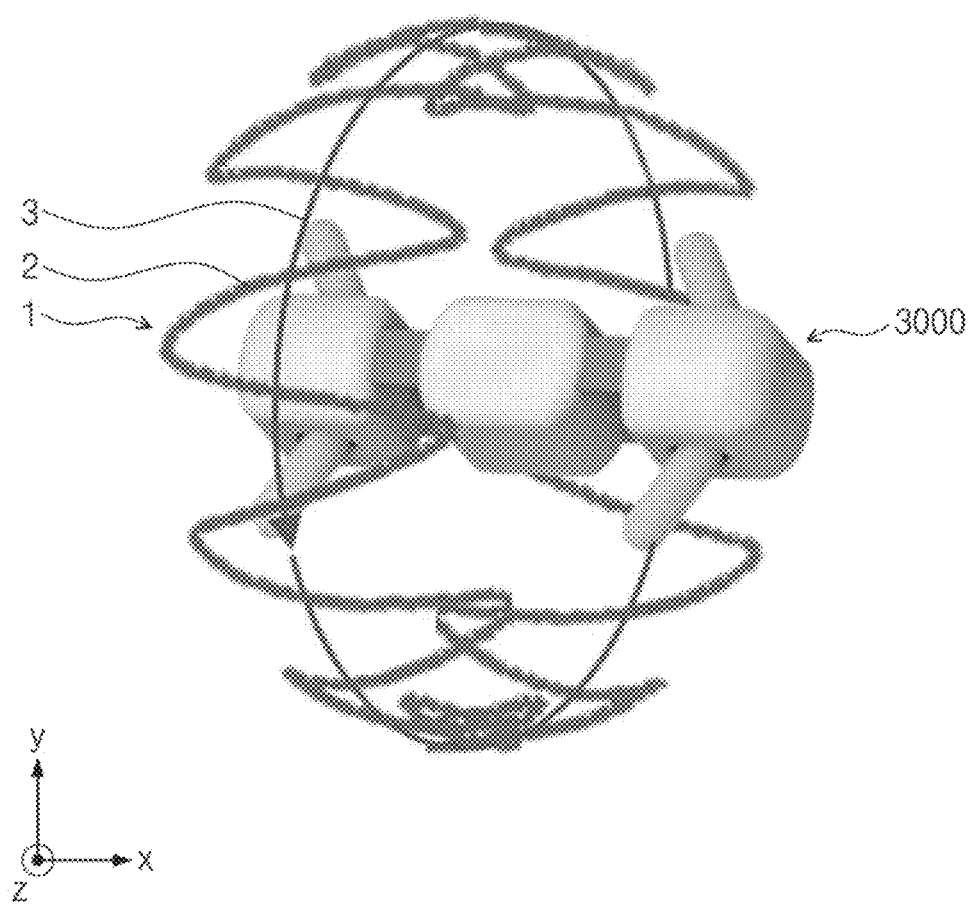
FIG. 14 is a view illustrating an example of applying an external magnetic field according to an embodiment of the present invention.
Figure 15:
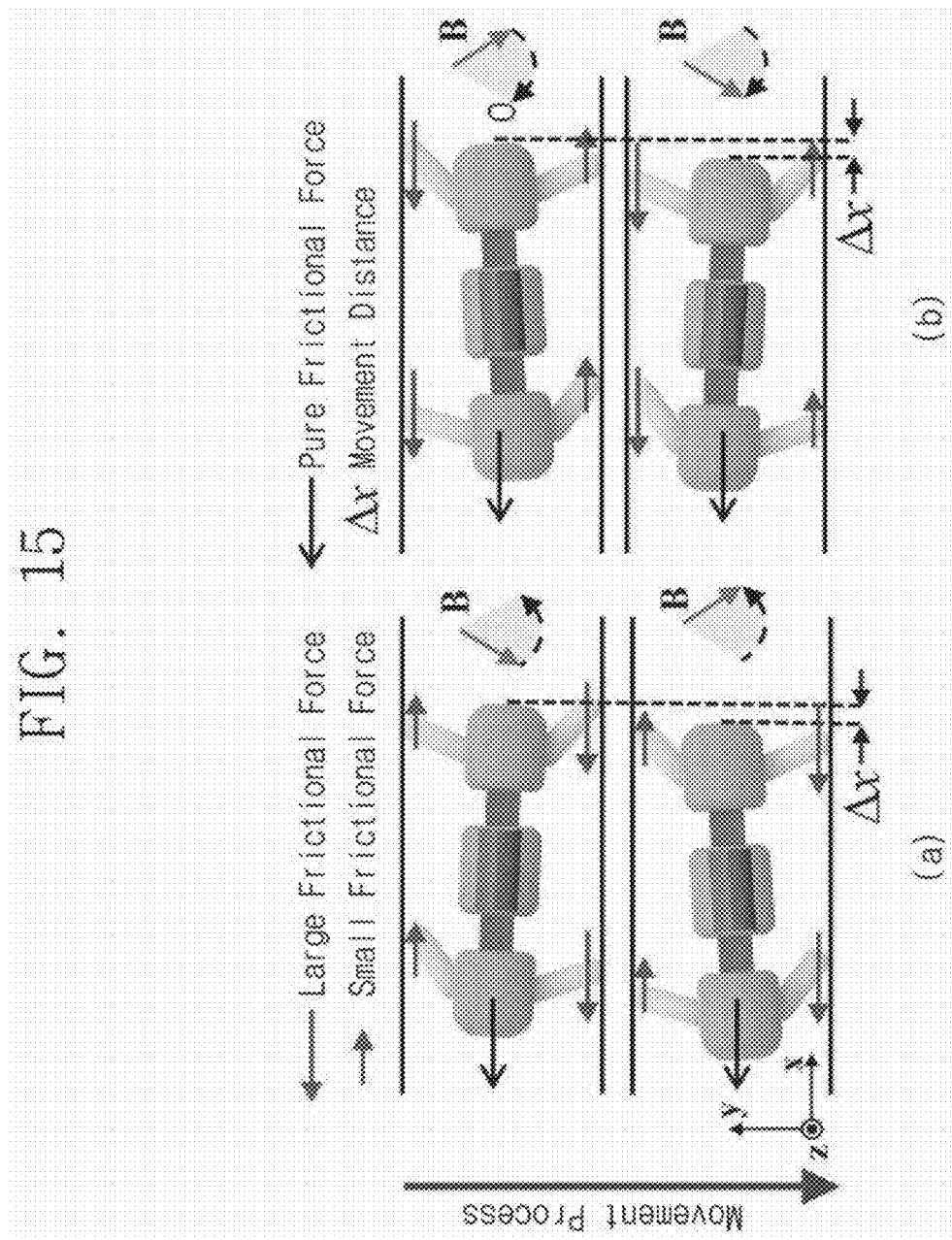
FIG. 15 is a view illustrating a motion of a moving robot according to a rotational direction of a vibrational magnetic field.

FIG. 14 is a view illustrating an example of applying an external magnetic field according to an embodiment of the present invention. FIG. 15 is a view illustrating a motion of a moving robot according to a rotational direction of a vibrational magnetic field. (A) represents a process of moving a moving robot by a vibrational magnetic field that is rotating in the counterclockwise direction, and (B) represents a process of moving a moving robot by a vibrational magnetic field that is rotated in the clockwise direction.

Referring to FIGS. 14 and 15, the external magnetic field 1 is provided such that the vibrational magnetic field 2 that is vibrating in a direction that is parallel to the XY plane rotates by 360° in the clockwise or counterclockwise direction 3 along a circumference of the moving robot 3000.

As illustrated in FIG. 15A, when the vibrational magnetic field 2 rotates in the counterclockwise direction, a frictional force between an upper leg of the moving robot 3000 and a pipe wall of the moving robot 3000 is smaller than a frictional force between a lower leg of the moving robot 3000 and the pipe wall of the moving robot 3000. Then, the moving robot moves forwards by a distance of Δx.

As illustrated in FIG. 15B, when the vibrational magnetic field 2 rotates in the clockwise direction, a frictional force between the upper leg of the moving robot 3000 and a pipe wall is larger than a frictional force between the lower leg of the moving robot 3000 and the pipe wall. In this case, the moving robot 3000 also moves forwards by a distance of Δx.

The vibrational magnetic field 3 that causes the motion is expressed as in Equation 2.

$$\vec{B}_{EOMF}(t) = B_0 \begin{bmatrix} \sin(\alpha \sin 2\pi f_1 t) \\ 0 \\ \cos(\alpha \sin 2\pi f_1 t) \end{bmatrix} \quad \text{[Equation 2]}$$

Here, $B_0$ is an intensity of an external magnetic field, a is a maximum rotation angle for vibration of an external magnetic field, and $f_1$ is a vibrational frequency.

Meanwhile, the movement performance of the moving robot 300 decreases when the vibrational magnetic field 2 is not generated in parallel to the XY plane, and the motion of the moving robot 3000 is not generated when the vibrational magnetic field 2 is generated perpendicularly to the XY plane.

In a plane, such as the XY plane, on which the moving robot 3000 may show a maximum driving performance, different vibrational magnetic fields have to be generated according to posture changes when the moving robot 3000 rotates while not taking a specific posture, such as in a bent pipe or a complex pipe. Then, vibrational magnetic fields 2 have to be changed through a precise and immediate reaction, which is very difficult to be achieved manually and causes an increase of moving time.

In this case, if a vibrational magnetic field 2 is generated while the moving robot 300 is compulsorily rotated by a magnetic field that rotates within a range of 180° to 360°, the moving robot 3000 moves while rotating and may be controlled to show a specific movement performed simply regardless of a posture of the moving robot 3000. The rotating vibrational magnetic field 2 may be expressed in Equation 3.

$$\vec{B}_{EORMF}(t) = B_0 \begin{bmatrix} \sin(\alpha \sin 2\pi f_1 t) \\ \cos(\alpha \sin 2\pi f_1 t)\cos 2\pi f_2 t \\ \cos(\alpha \sin 2\pi f_1 t)\sin 2\pi f_2 t \end{bmatrix}$$ [Equation 3]

Here, $f_2$ is a rotational frequency of an external magnetic field.

Figure 16:
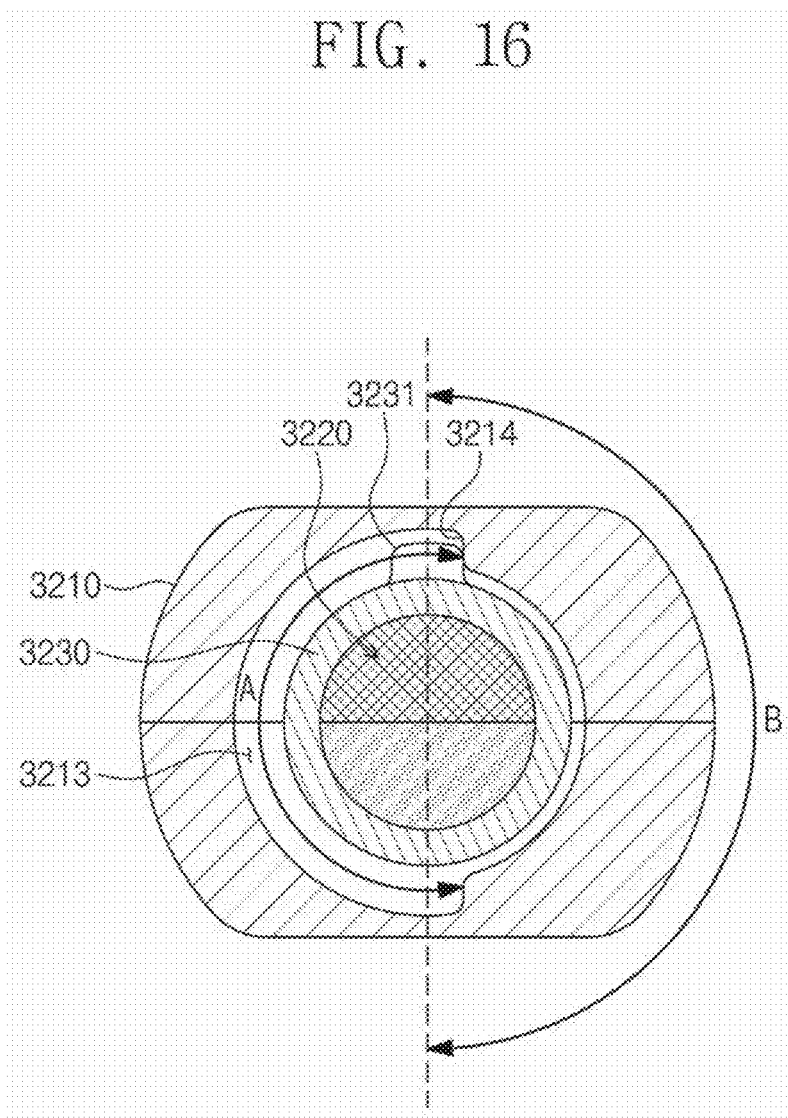
FIG. 16 is a view illustrating a process of rotating the moving robot according to a vibrational magnetic field that is rotating.

FIG. 16 is a view illustrating a process of rotating the moving robot according to a vibrational magnetic field that is rotating.

Referring to FIG. 16, the movable magnet 3220 is rotated by a torque generated by the rotating vibrational magnetic field 2. In detail, the movable magnet 3220 and the movable magnet cover 3230 rotate in a rotation range A of 180° to 360° while the moving boss 3231 moves along the guide groove 3213. In a rotation range B of 180° to 360°, the stopping boss 3231 is stopped by the stopping step 3214 and the movable magnet cover 3230 and the movable body 3210 are rotated together by a rotational force of the movable magnet 3220. Accordingly, the entire moving robot 3000 may be compulsorily rotated.

Figure 17:
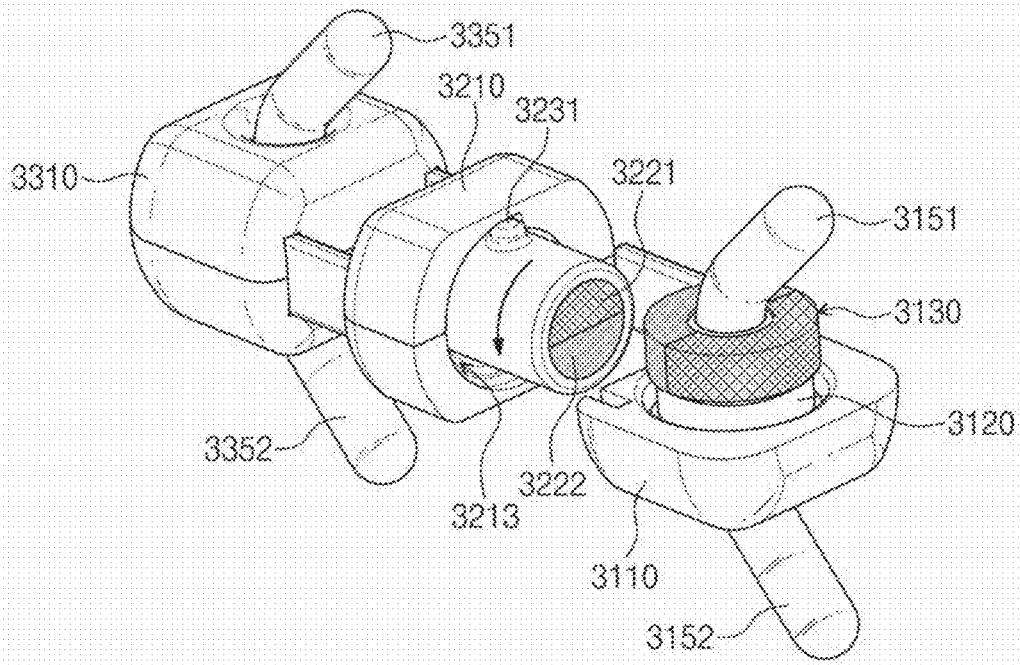
FIGS. 17 to 19 are views sequentially illustrating processes of the moving robot changing a movement direction according to an external magnetic field.
Figure 18:
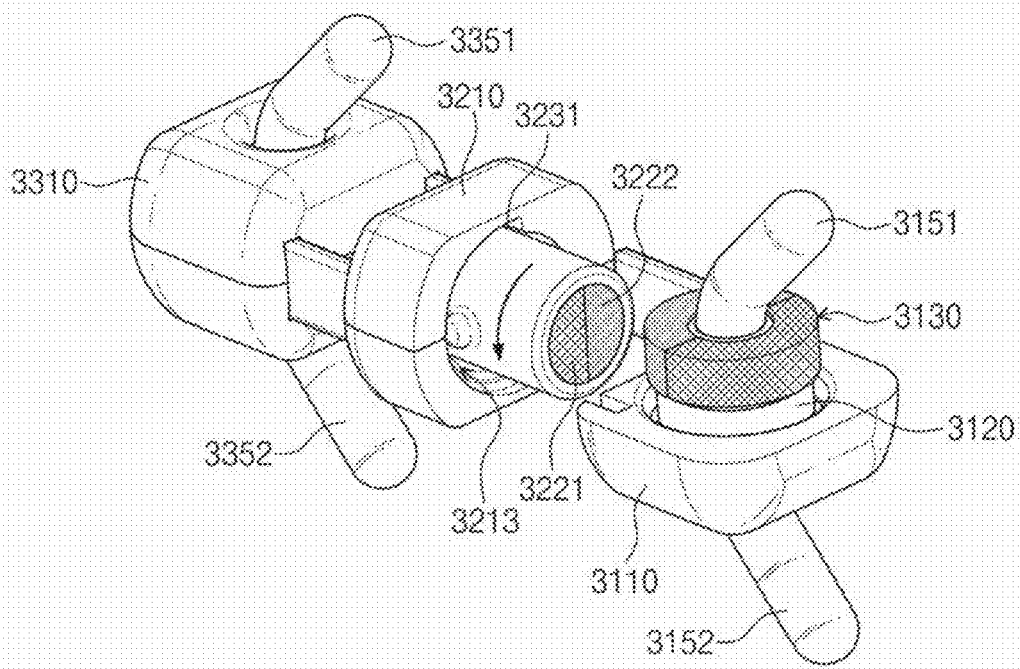
Figure 19:
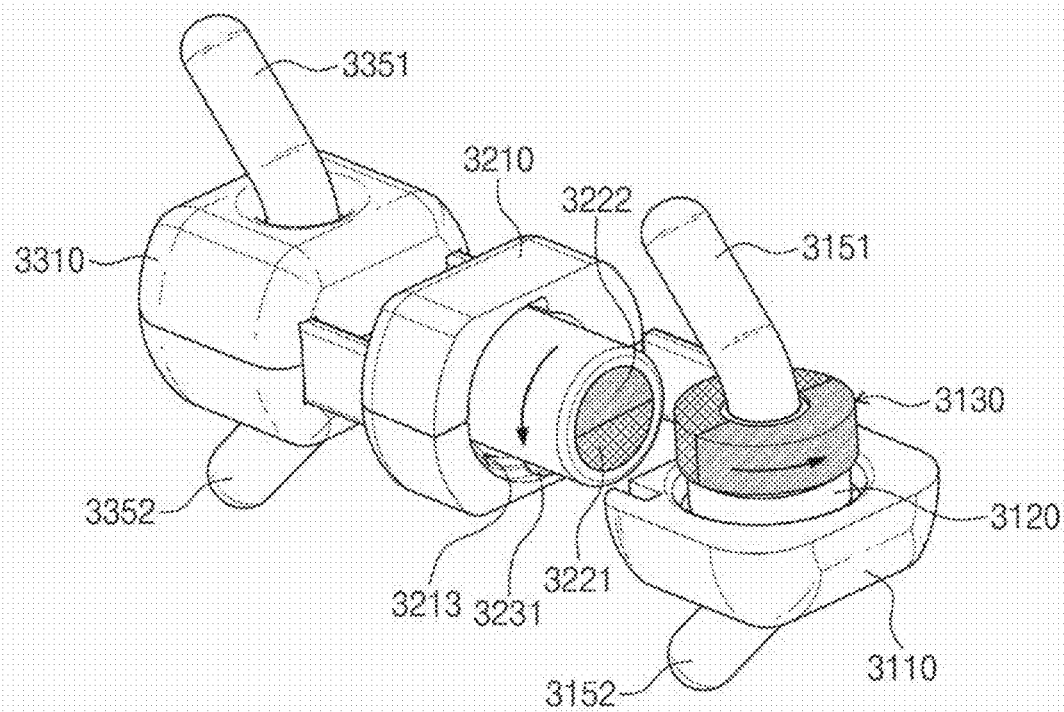
Figure 20:
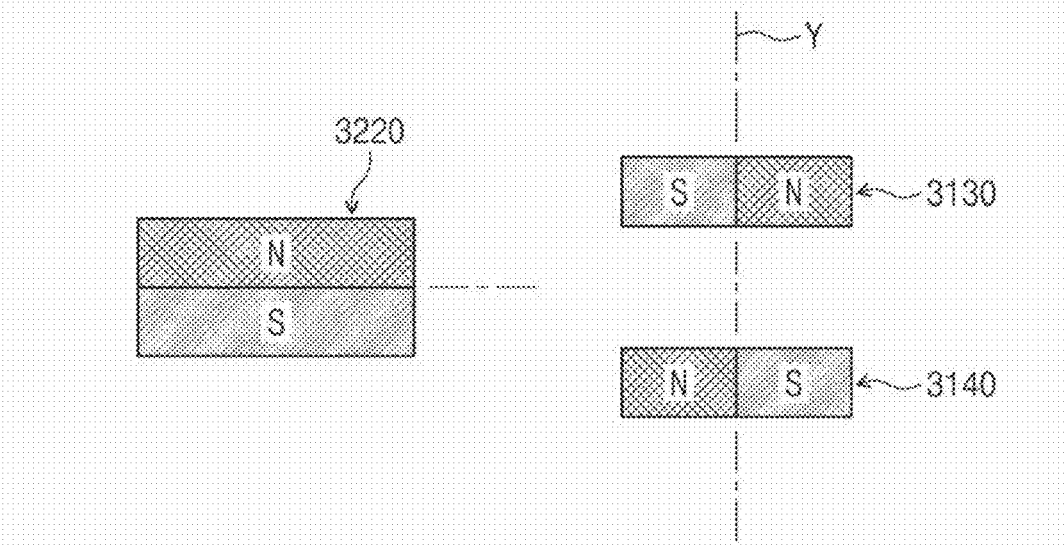
FIG. 20 is a view illustrating a disposal relationship of steering magnets and a movable magnet of the moving robot of FIG. 17.
Figure 21:
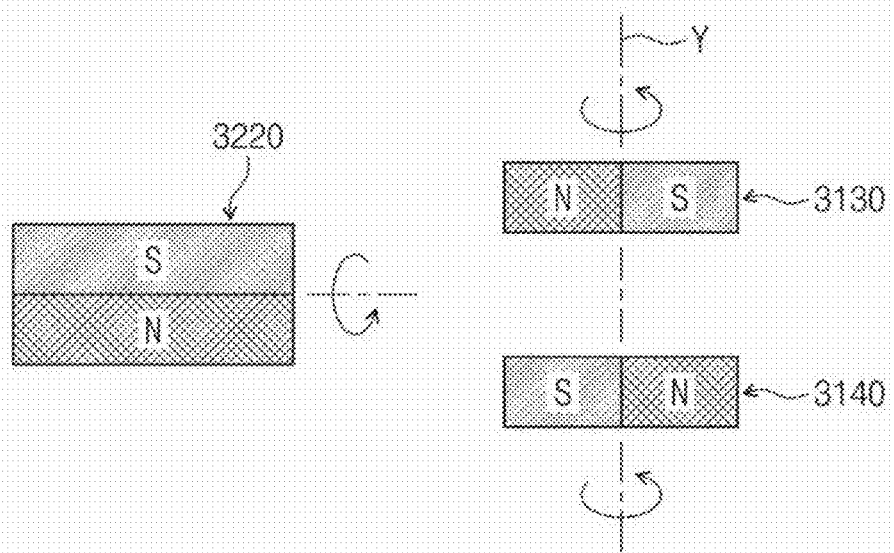
FIG. 21 is a view illustrating a disposal relationship of steering magnets and a movable magnet of the moving robot of FIG. 19.

FIGS. 17 to 19 are views sequentially illustrating processes of the moving robot changing a movement direction according to an external magnetic field. FIG. 20 is a view illustrating a disposal relationship of steering magnets and a movable magnet of the moving robot of FIG. 17. FIG. 21 is a view illustrating a disposal relationship of steering magnets and a movable magnet of the moving robot of FIG. 19.

Referring to FIGS. 17 to 21, a direction of a pure frictional force that determines a movement direction may be influenced by inclination directions of the legs 3151, 3152, 3351, and 3352, and the forward/rearward direction of the moving robot 3000 may be switched through reversing of the inclination directions of the legs 3151, 3152, 3351, and 3352.

As described above, because the sum of the magnetic moments of the first steering magnet 3130 and the second steering magnet 3140 is 0, the moving robot 3000 is not influenced by an external magnet and is influenced only by an attractive force and a repulsive force of the movable magnet 3220.

The magnetic force of one pole of the movable magnet 3220 influences the first steering magnet 3130, and the magnetic force of an opposite pole of the movable magnet 3220 influences the second steering magnet 3140. If the movable magnet 3220 rotates within a rotation range of 0° to 180°, magnetic torques are applied to the steering magnets 3130 and 3140 by the repulsive forces with the movable magnet 3220 and the steering magnets 3130 and 3140 are rotated about the first direction Y. As the steering magnets 3130 and 3140 rotate, the spacer 3120 and the legs 3151, 3152, 3351, and 3352 attached to the spacer 3120 rotate, and the movement direction of the moving robot 3000 is changed as the inclination directions of the legs 3151, 3152, 3351, and 3352 are changed.

Figure 22:
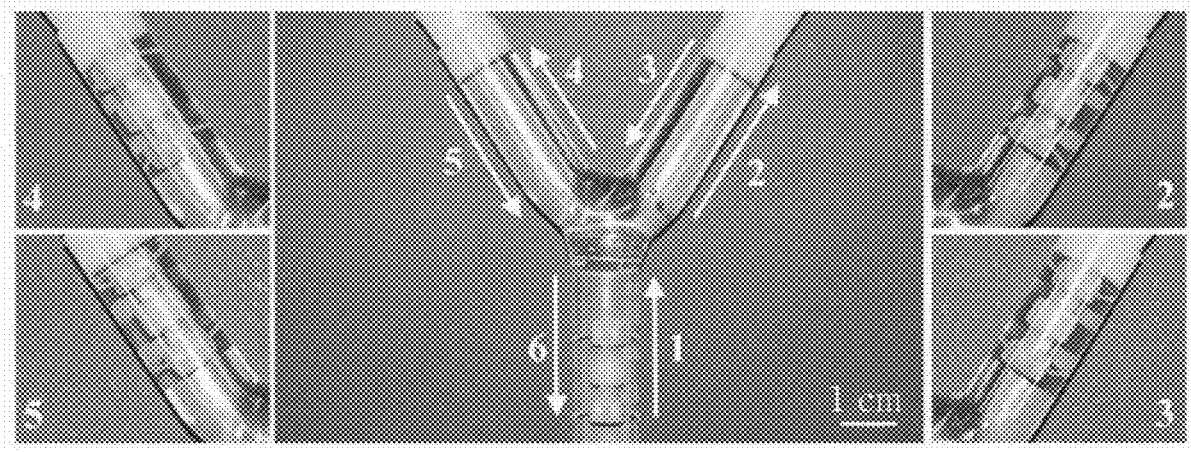
FIG. 22 is an experimental picture illustrating a movement and directional switching of the moving robot in a Y-shaped branch pipe according to the embodiment of the present invention.

FIG. 22 is an experimental picture illustrating a movement and directional switching of the moving robot in a Y-shaped branch pipe according to the embodiment of the present invention.

Referring to FIG. 22, the moving robot used in the experiment has a maximum width of 13 mm and a length of 27 mm. The picture shows an appearance in which the moving robot moves and switches a direction thereof with a rotating vibrational magnetic field of 14 mT in the Y-shaped branch pipe. The vibrational angle, the vibrational frequency, and the rotational frequency that are external magnetic field generating parameters were 60 degrees, 8 Hz, and 10 Hz. The direction of the devised moving robot was switched by bending the rotational axis of the rotating vibrational magnetic field when the moving robot moved from process 1 to process 2, and the inclination directions of the legs were changed by using the above-described direction switching method when the moving robot moved from process 2 to process 3. In the same method, The moving robot returns to the original position after circulating the Y-shaped branch pipe through a scheme of bending the rotational axis of the vibrational magnetic field and switching the inclination angles of the legs.

Figure 23A:
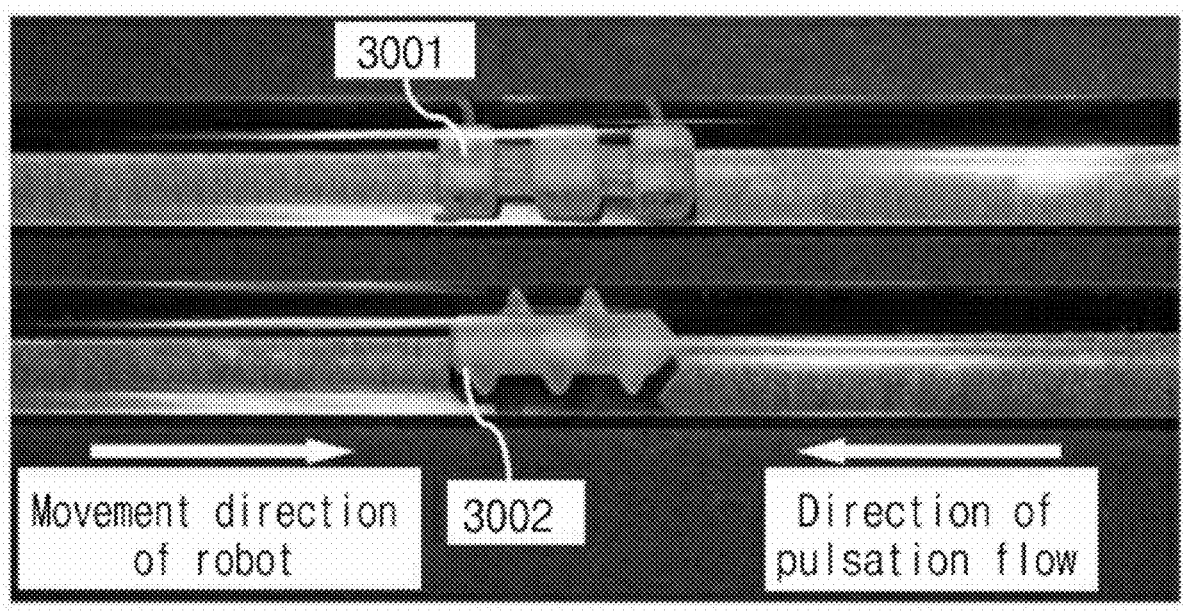
FIGS. 23A to 23C are experimental pictures obtained by comparing motions of the moving robot of the present invention and a rotary magnetic robot that is a comparison target in a straight pipe and result graphs thereof.
Figure 23B:
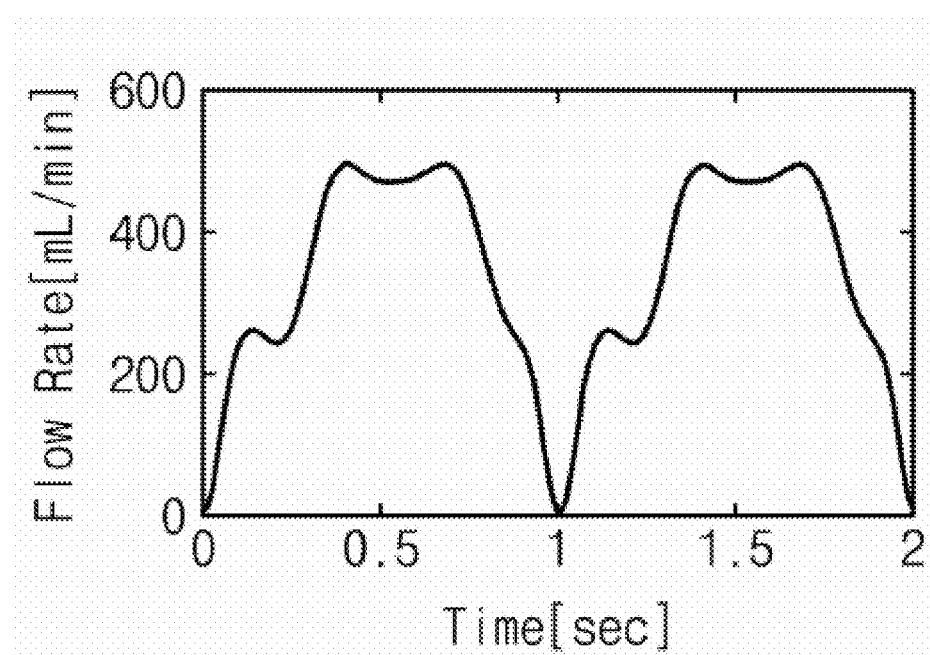
Figure 23C:
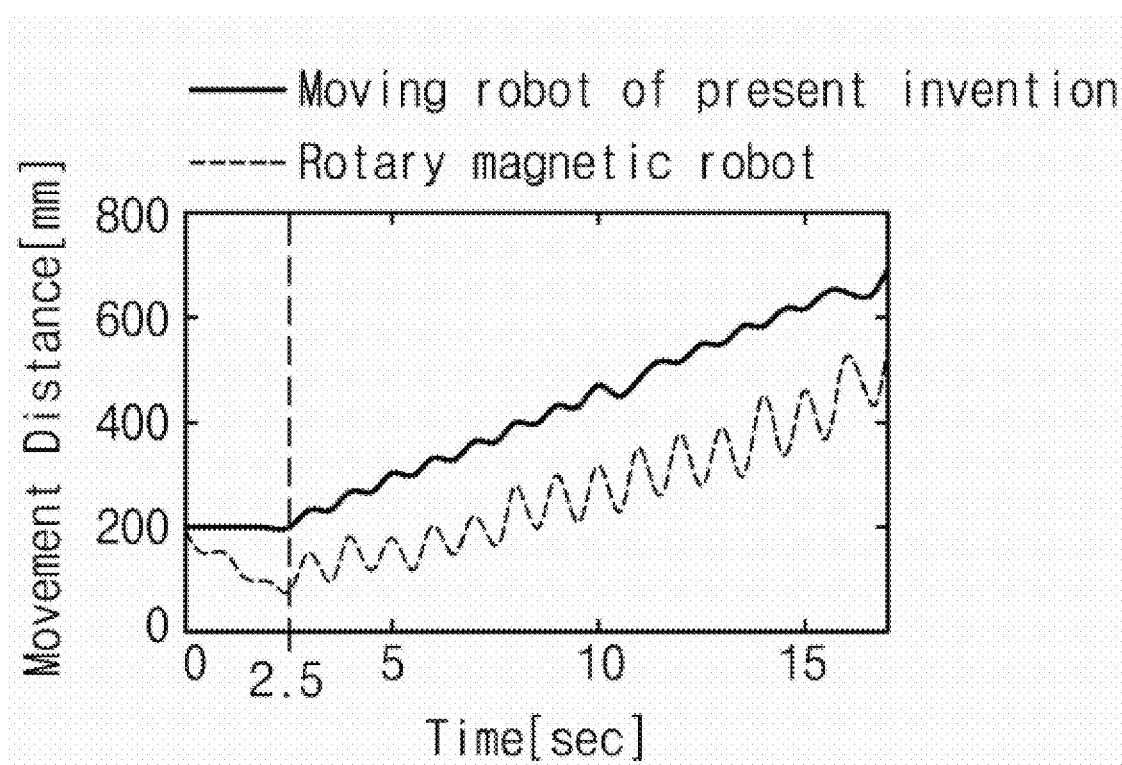

FIGS. 23A to 23C are experimental pictures obtained by comparing motions of the moving robot of the present invention and a rotary magnetic robot that is a comparison target in a straight pipe and result graphs thereof. The experiment was performed by generating a pulsation flow in a straight pipe. FIG. 23A is a picture that represents an appearance in which the moving robot 1 of the present invention and a rotary magnetic robot 2 move in a straight pipe. FIG. 23B is a graph that depicts a change of flow rate according to a time of the pulsation flow applied to the straight pipe. FIG. 23C is a graph that depicts movement distances of the robots 3001 and 3002 according to time.

The moving robot 3001 employed the external magnetic field generating parameters suggested above, and the rotary magnetic robot 3002 employed a rotating magnetic field of 9 Hz. The two robots 3001 and 3002 were not controlled by an external magnetic field at 0 to 2.5 seconds, and were controlled by an external magnetic field until 17 seconds after then. It may be seen from the measurement result that as compared with the rotary magnetic robot 3002 that was pushed by the pulsation flow when there is no control by an external magnetic field, the moving robot 3001 stably maintained its position. Further, as compared with the rotary magnetic robot 3002 that causes a change of position according to a pulsation frequency when there is a control by an external magnetic field, the moving robot 3001 of the present invention showed a relatively stable position increase without being pushed backwards.

Figure 24:
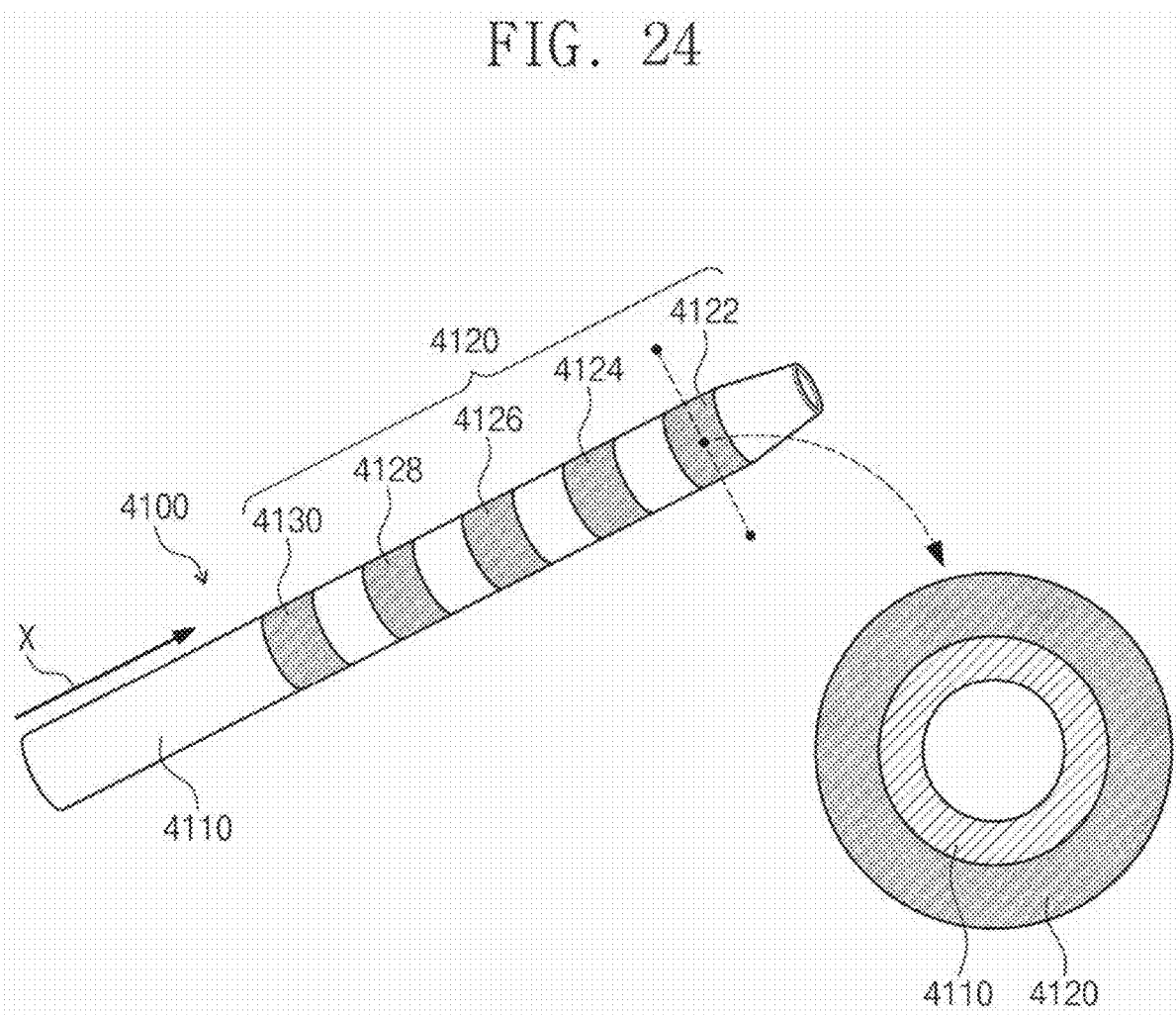
FIG. 24 is a view illustrating a magnetic tube system according to an embodiment of the present invention.

FIG. 24 is a view illustrating a magnetic tube system according to an embodiment of the present invention.

Referring to FIG. 24, the magnetic tube system 4100 includes a tube 4110 and a magnetic part 4120.

The tube 4110 has a pipe shape having a specific diameter and is formed of a flexible material.

The magnetic part 4120 may be inserted into the tube 4110, and may deform of the form of the tube 4110 such that the direction of the magnetic moment is arranged with the direction of the magnetic force generated by an external magnetic field. The magnetic part 4120 may include two or more magnetic bodies 4122, 4124, 4126, 4128, and 4130. The magnetic bodies may be sequentially inserted in the lengthwise direction X of the tube 4110. The magnetic bodies may be inserted while maintaining a specific distance.

According to an embodiment, the directions of the magnetic moments of the magnetic bodies may be different. The direction of the moment of any one of the two or more magnetic bodies, of which directions of the magnetic moments are different, is the same as the lengthwise direction X of the tube 4110, and the direction of the moment of another one of the two or more magnetic bodies may form a specific angle with the lengthwise direction X of the tube 4110. Another one of the two or more magnetic bodies may have a magnetic moment of a direction that is opposite to the direction of the magnetic moment of the magnetic body, of which the direction of the moment is the same as the lengthwise direction X of the tube 4110.

According to an embodiment, the magnitudes of the magnetic moments of the magnetic bodies may be different. The magnitude of the magnetic moment of any one of the two or more magnetic bodies, of which the magnitudes of the magnetic moments are different, may be greater than the magnitude of the magnetic moment of another magnetic body.

When an external magnetic field is applied to the above-described magnetic tube system 4100, a magnetic force and a magnetic torque applied to the magnetic part 4120 inserted into the magnetic tube system 4100 by the external magnetic field may be expressed in the following equation.

$$\overline{T}=\overline{m}\times\overline{B} \quad (4)$$

$$\overline{F}=-\nabla(\overline{m}\cdot\overline{B}) \quad (5)$$

Here, $\overline{m}$ is a magnetic moment of the magnetic part 4120 and $\overline{B}$ is a magnetic flux density of the external magnetic field.

The magnetic force and the magnetic torque applied to the magnetic part 4120 inserted into the magnetic tube system 4100 may be calculated by Equations 4 and 5.

When the intensity of the magnetic torque applied to the magnetic part 4120 by the external magnetic field is higher than the elastic force of the tube 4110, the tube 4110 may be deformed such that the direction of the magnetic moment of the magnetic part 4120 coincides with the direction of the magnetic field of the external magnetic field.

Hereinafter, various embodiments of the above-described magnetic tube system will be described. It is described in the embodiments that the magnetic part 4120 includes five magnetic bodies 4122, 4124, 4126, 4128, and 4130, but the number of the magnetic bodies may be variously changed.

Figure 25:
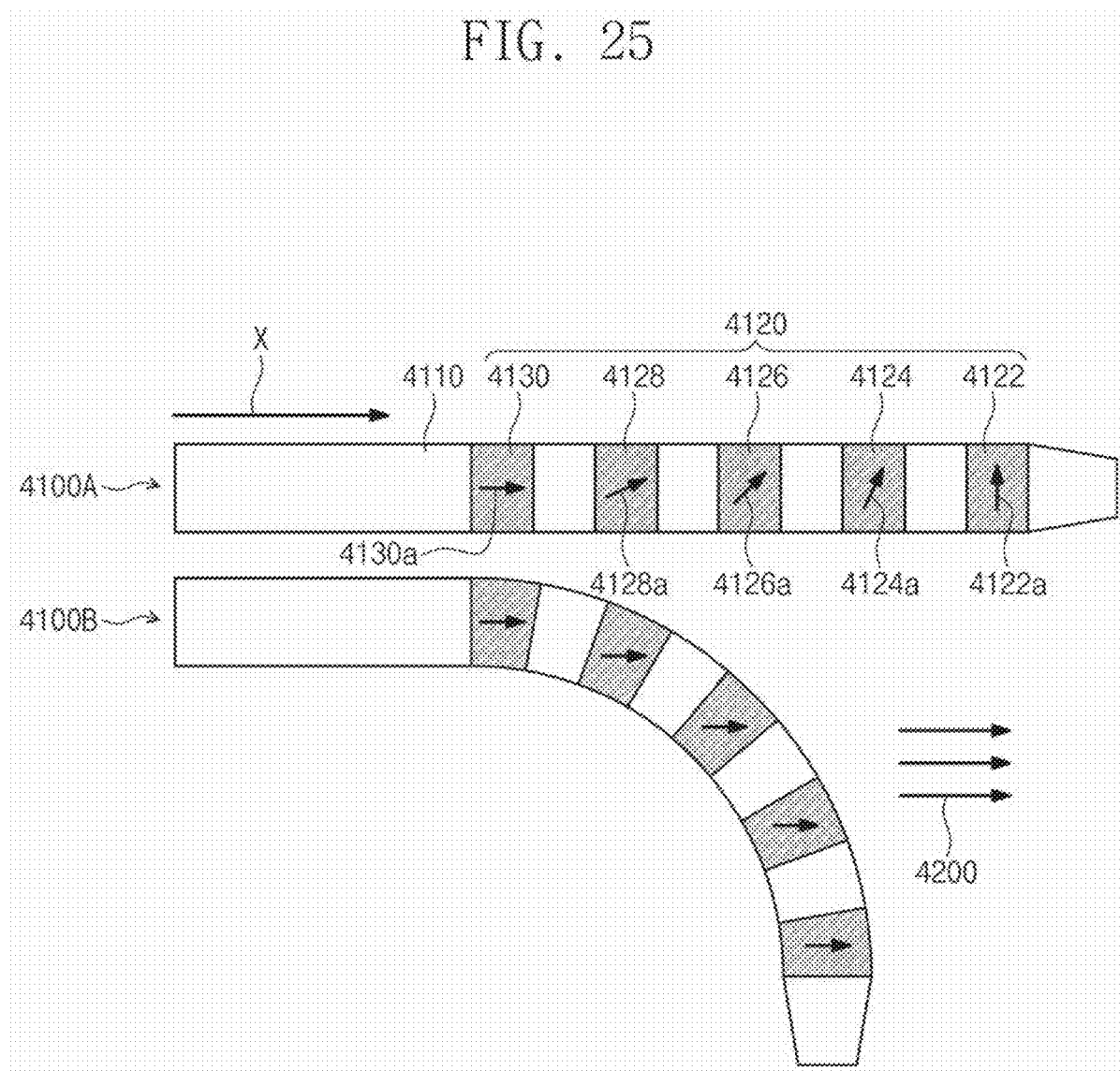
FIG. 25 is a view illustrating a magnetic tube system according to a first embodiment of the present invention.

FIG. 25 is a view illustrating a magnetic tube system according to a first embodiment of the present invention. Reference numeral 4100A denotes the magnetic tube system before an external magnetic field is applied, and reference numeral 4100B denotes a deformed form of the magnetic tube system according to the application of the external magnetic field.

First, referring to 4100A of FIG. 25, the magnetic tube system 4100 includes a tube 4100 and first to fifth magnetic bodies 4122, 4124, 4126, 4128, and 4130 inserted into the tube 4100.

The directions of the magnetic moments 4122a, 4124a, 4126a, 4128a, and 4130a of the first to fifth magnetic bodies 4122, 4124, 4126, 4128, and 4130 inserted into the tube 4100 of the magnetic tube system 4100A may be different and the magnitudes of the magnetic moments 4122a, 4124a, 4126a, 4128a, and 4130a may be the same.

The direction of the magnetic moment 4122a of the first magnetic body 4122 is perpendicular to the lengthwise direction X of the tube 4110, the direction of the magnetic moment 4126a of the third magnetic body 4126 forms a degree of 45° with the lengthwise direction X of the tube 4110, and the direction of the magnetic moment 4130a of the fifth magnetic body 4130 may be the same as the lengthwise direction X of the tube 4100. The direction of the magnetic moment 4124a of the second magnetic body 4124 may form a specific angle with the lengthwise direction X of the tube 4110 in a range between the direction of the magnetic moment 4122a of the first magnetic body 4122 and the direction of the magnetic moment 4126a of the third magnetic body 4126, and the direction of the magnetic moment 4128a of the fourth magnetic body 4128 may form a specific angle with the lengthwise direction X of the tube 4110 in a range between the direction of the magnetic moment 4126a of the third magnetic body 4126 and the direction of the magnetic moment 4130a of the fifth magnetic body 4130. According to an embodiment, the direction of the magnetic moment 4124a of the second magnetic body 4124 may form a degree of 67.5° with the lengthwise direction X of the tube 4110, and the direction of the magnetic moment 4128a of the fourth magnetic body 4128 may form a degree of 22.5° with the lengthwise direction of the tube 4110.

Referring to 4100B of FIG. 25, when the direction of the magnetic force generated by an external magnetic field is the same as the lengthwise direction X of the tube 4110, the first to fifth magnetic bodies 4122, 4124, 4126, 4128, and 4130 receives a magnetic torque from the external magnetic field such that the directions of the magnetic moments 4122a, 4124a, 4126a, 4128a, and 4130a coincide with the direction of the magnetic force of the external magnetic field.

In detail, the first magnetic body 4122 deforms the tube 4110 while rotating clockwise by 90° such that the direction of the magnetic moment 4122a coincides with the direction of the magnetic field of the external magnetic field 4200. The second magnetic body 4124 deforms the tube 4110 while rotating clockwise by 67.5° such that the direction of the magnetic moment 4124a coincides with the direction of the magnetic field of the external magnetic field 4200. The third magnetic body 4126 deforms the tube 4110 while rotating clockwise by 45° such that the direction of the magnetic moment 4126a coincides with the direction of the magnetic field of the external magnetic field 4200. The fourth magnetic body 4128 deforms the tube 4110 while rotating clockwise by 22.5° such that the direction of the magnetic moment 4128a coincides with the direction of the magnetic field of the external magnetic field 4200. The fifth magnetic body 4130 does not deform the tube 4110 as the direction of the magnetic moment 4130a coincides with the direction of the magnetic field of the external magnetic field 4200.

The tube 4110 may be bent such that an end of the tube 4110 may face the lower side by arranging the first to fifth magnetic bodies 4122, 4124, 4126, 4128, and 4130.

Figure 26:
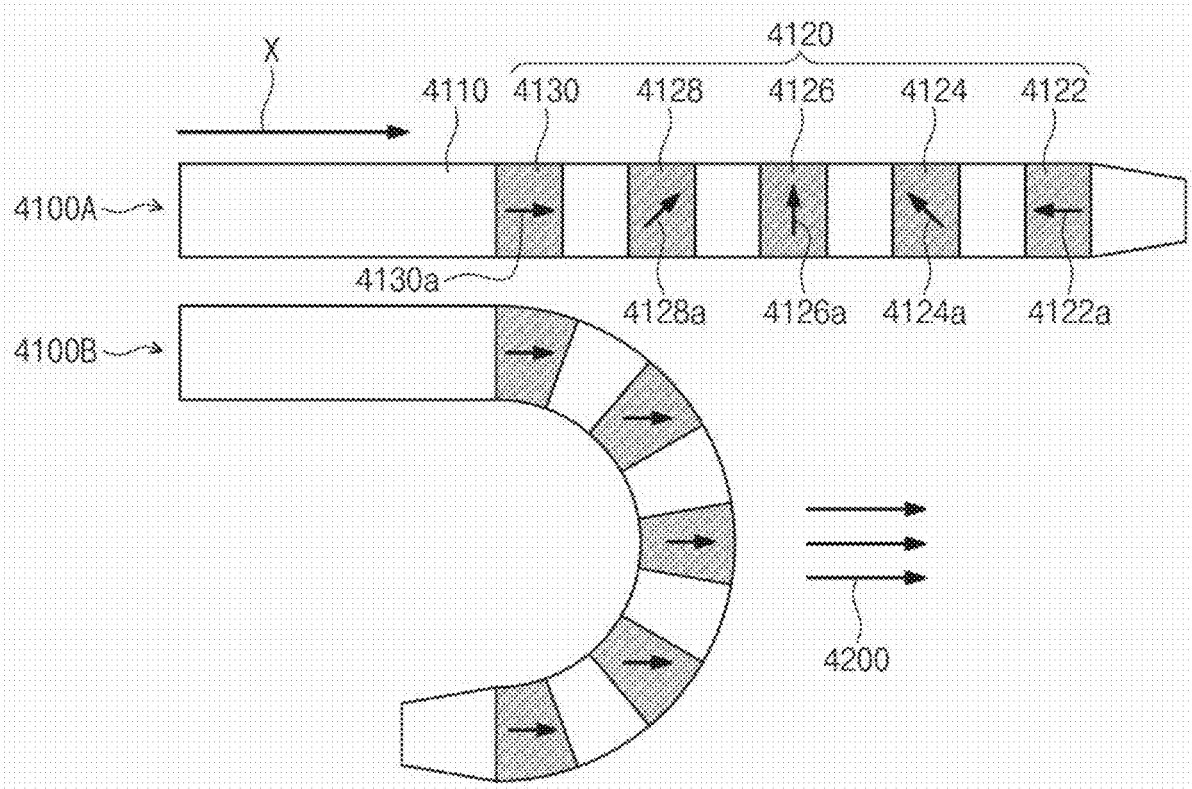
FIG. 26 is a view illustrating a magnetic tube system according to a second embodiment of the present invention.

FIG. 26 is a view illustrating a magnetic tube system according to a second embodiment of the present invention. Reference numeral 4100A denotes the magnetic tube system before an external magnetic field is applied, and reference numeral 4100B denotes a deformed form of the magnetic tube system according to the application of the external magnetic field.

Referring to FIG. 26, the magnetic tube system 4100 includes a tube 4100 and first to fifth magnetic bodies 4122, 4124, 4126, 4128, and 4130 inserted into the tube 4100.

The directions of the magnetic moments 4122a, 4124a, 4126a, 4128a, and 4130a of the first to fifth magnetic bodies 4122, 4124, 4126, 4128, and 4130 inserted into the tube 4100 of the magnetic tube system 4100A may be different and the magnitudes of the magnetic moments 4122a, 4124a, 4126a, 4128a, and 4130a may be the same.

The direction of the magnetic moment 4122a of the first magnetic body 4122 is opposite to the lengthwise direction X of the tube 4110, the direction of the magnetic moment 4124a of the second magnetic body 4124 may form an angle of 135° with the lengthwise direction of the tube 4110, the direction of the magnetic moment 4126a of the third magnetic body 4126 is perpendicular to the lengthwise direction X of the tube 4110, the direction of the magnetic moment 4128a of the fourth magnetic body 4128 may form an angle of 45° with the lengthwise direction of the tube 4110, and the direction of the magnetic moment 4130a of the fifth magnetic body 4130 is the same as the lengthwise direction X of the tube 4110.

Referring to 4100B of FIG. 26, when the direction of the magnetic force generated by an external magnetic field is the same as the lengthwise direction X of the tube 4110, the first to fifth magnetic bodies 4122, 4124, 4126, 4128, and 4130 receives a magnetic torque from the external magnetic field such that the directions of the magnetic moments 4122a, 4124a, 4126a, 4128a, and 4130a coincide with the direction of the magnetic force of the external magnetic field.

In detail, the first magnetic body 4122 deforms the tube 4110 while rotating clockwise by 180° such that the direction of the magnetic moment 4122a coincides with the direction of the magnetic field of the external magnetic field 4200. The second magnetic body 4124 deforms the tube 4110 while rotating clockwise by 135° such that the direction of the magnetic moment 4124a coincides with the direction of the magnetic field of the external magnetic field 4200. The third magnetic body 4126 deforms the tube 4110 while rotating clockwise by 90° such that the direction of the magnetic moment 4,126a coincides with the direction of the magnetic field of the external magnetic field 4200. The fourth magnetic body 4128 deforms the tube 4110 while rotating clockwise by 45° such that the direction of the magnetic moment 4,128a coincides with the direction of the magnetic field of the external magnetic field 4200. The fifth magnetic body 4130 does not deform the tube 4110 as the direction of the magnetic moment 4130a coincides with the direction of the magnetic field of the external magnetic field 4200.

The tube 4110 may be bent to have a C shape by arranging the first to fifth magnetic bodies 4122, 4124, 4126, 4128, and 4130.

Figure 27:
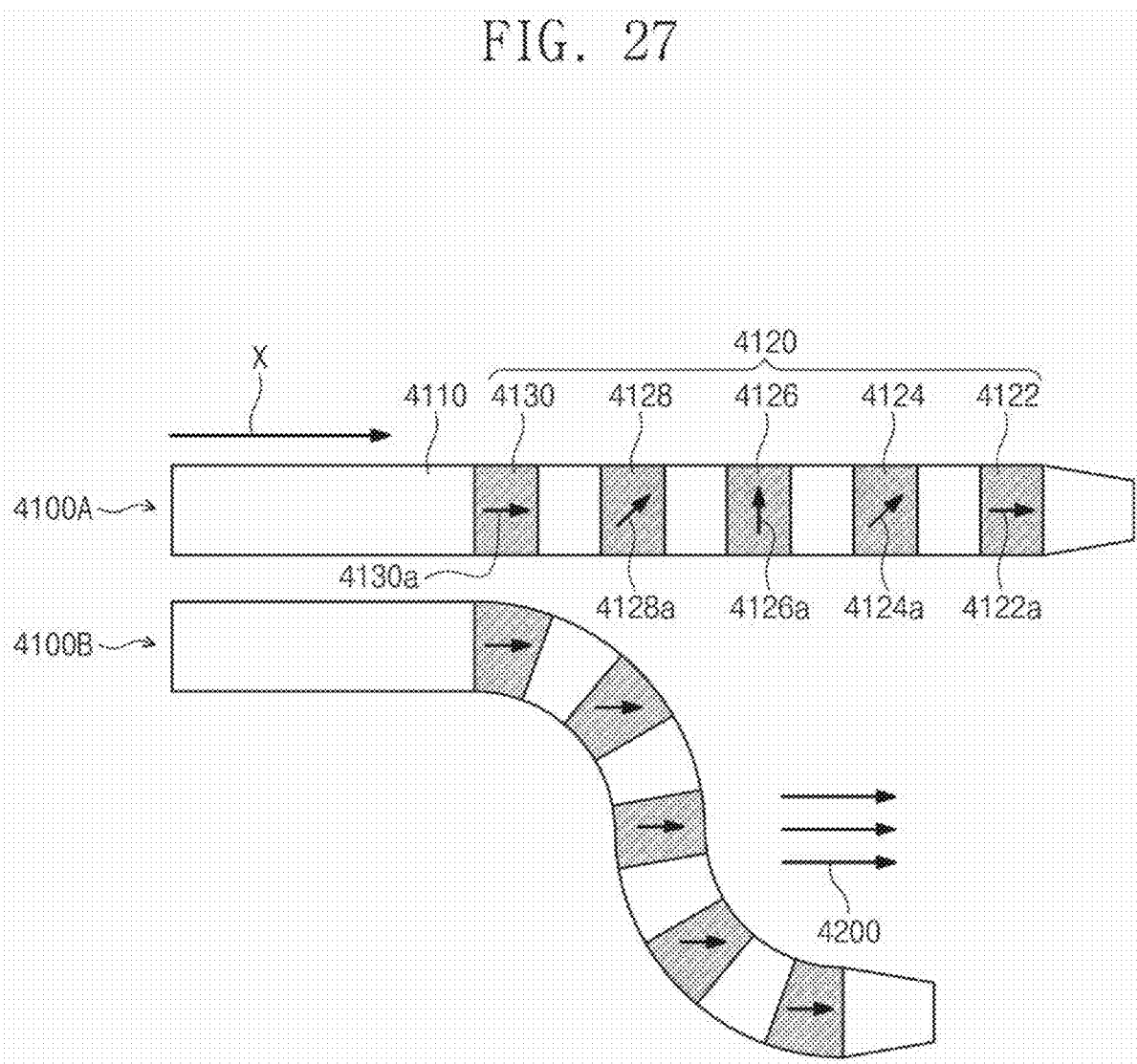
FIG. 27 is a view illustrating a magnetic tube system according to a third embodiment of the present invention.

FIG. 27 is a view illustrating a magnetic tube system according to a third embodiment of the present invention. Reference numeral 4100A denotes the magnetic tube system before an external magnetic field is applied, and reference numeral 4100B denotes a deformed form of the magnetic tube system according to the application of the external magnetic field.

Referring to FIG. 27, the magnetic tube system 4100 includes a tube 4100 and first to fifth magnetic bodies 4122, 4124, 4126, 4128, and 4130 inserted into the tube 4100.

The directions of the magnetic moments 4122a, 4124a, 4126a, 4128a, and 4130a of the first to fifth magnetic bodies 4122, 4124, 4126, 4128, and 4130 inserted into the tube 4100 of the magnetic tube system 4100A may be different and the magnitudes of the magnetic moments 4122a, 4124a, 4126a, 4128a, and 4130a may be the same.

The directions of the magnetic moments 4122a and 4130a of the first magnetic body 4122 and the fifth magnetic body 4130 are the same as the lengthwise direction X of the tube 4110, the directions of the magnetic moments 4124a and 4128a of the second magnetic body 4124 and the fourth magnetic body 4128 form a degree of 45° with the lengthwise direction X of the tube 4110, and the direction of the magnetic moment 4126a of the third magnetic body 4126 is perpendicular to as the lengthwise direction X of the tube 4100.

Referring to 4100B of FIG. 27, when the direction of the magnetic force generated by an external magnetic field is the same as the lengthwise direction X of the tube 4110, the first to fifth magnetic bodies 4122, 4124, 4126, 4128, and 4130 receives a magnetic torque from the external magnetic field such that the directions of the magnetic moments 4122a, 4124a, 4126a, 4128a, and 4130a coincide with the direction of the magnetic force of the external magnetic field.

In detail, the first magnetic body 4122 and the fifth magnetic body 4130 do not deform the tube 4110 as the directions of the magnetic moments 4122a and 4130a coincide with the direction of the magnetic field of the external magnetic field 4200. The second magnetic body 4124 and the fourth magnetic body 4128 deform the tube 4110 while rotating clockwise by 45° such that the direction of the magnetic moments 4124a and 4128a coincide with the direction of the magnetic field of the external magnetic field 4200. The third magnetic body 4126 deforms the tube while rotating clockwise by 90° such that the direction of the magnetic moment 4,126a coincides with the direction of the magnetic field of the external magnetic field 4200.

The tube 4110 may be bent such that the direction of the tube 4110 is changed two times by arranging the first to fifth magnetic bodies 4122, 4124, 4126, 4128, and 4130.

Figure 28:
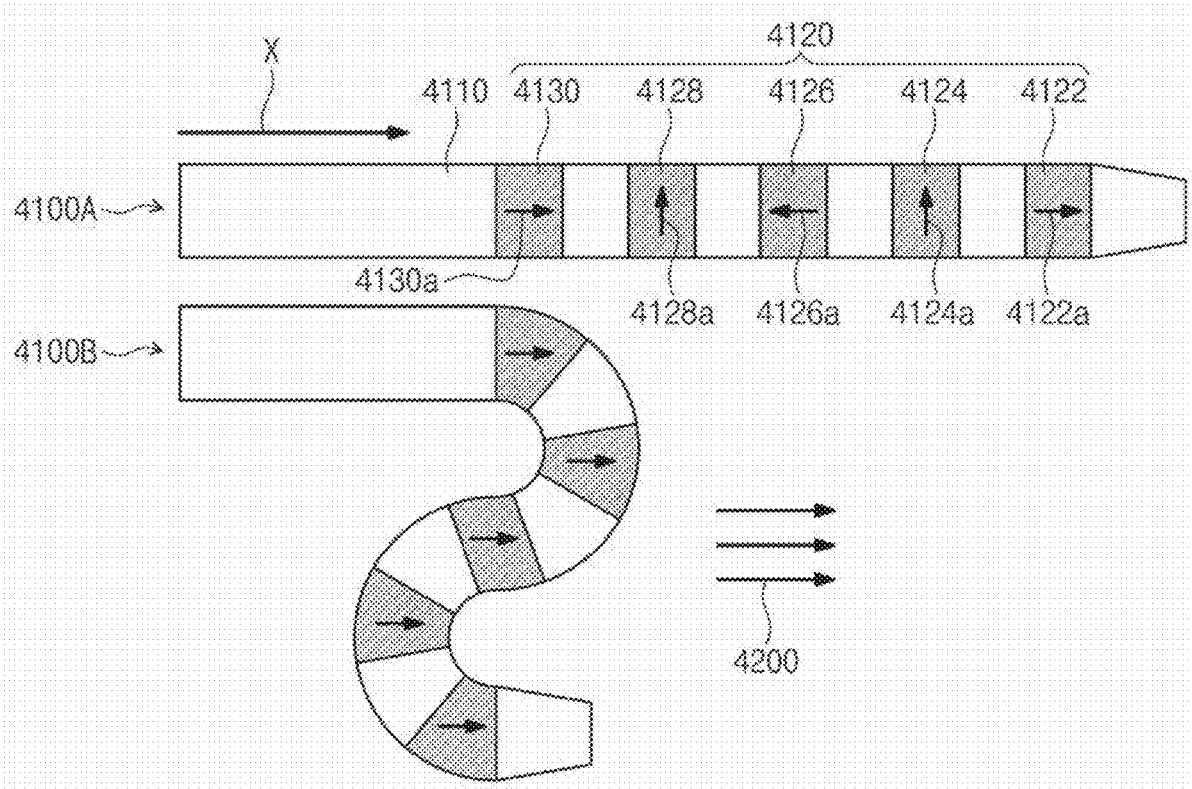
FIG. 28 is a view illustrating a magnetic tube system according to a fourth embodiment of the present invention.

FIG. 28 is a view illustrating a magnetic tube system according to a fourth embodiment of the present invention. Reference numeral 4100A denotes the magnetic tube system before an external magnetic field is applied, and reference numeral 4100B denotes a deformed form of the magnetic tube system according to the application of the external magnetic field.

Referring to FIG. 28, the magnetic tube system 4100 includes a tube 4100 and first to fifth magnetic bodies 4122, 4124, 4126, 4128, and 4130 inserted into the tube 4100.

The directions of the magnetic moments 4122a, 4124a, 4126a, 4128a, and 4130a of the first to fifth magnetic bodies 4122, 4124, 4126, 4128, and 4130 inserted into the tube 4100 of the magnetic tube system 4100A may be different and the magnitudes of the magnetic moments 4122a, 4124a, 4126a, 4128a, and 4130a may be the same.

The directions of the magnetic moments 4122a and 4130a of the first magnetic body 4122 and the fifth magnetic body 4130 are the same as the lengthwise direction X of the tube 4110, the directions of the magnetic moments 4124a and 4128a of the second magnetic body 4124 and the fourth magnetic body 4128 is perpendicular to the lengthwise direction X of the tube 4110, and the direction of the magnetic moment 4126a of the third magnetic body 4126 is opposite to as the lengthwise direction X of the tube 4100.

Referring to 4100B of FIG. 28, when the direction of the magnetic force generated by an external magnetic field is the same as the lengthwise direction X of the tube 4110, the first to fifth magnetic bodies 4122, 4124, 4126, 4128, and 4130 receives a magnetic torque from the external magnetic field such that the directions of the magnetic moments 4122a, 4124a, 4126a, 4128a, and 4130a coincide with the direction of the magnetic force of the external magnetic field.

In detail, the first magnetic body 4122 and the fifth magnetic body 4130 do not deform the tube 4110 as the directions of the magnetic moments 4122a and 4130a coincide with the direction of the magnetic field of the external magnetic field 4200. The second magnetic body 4124 and the fourth magnetic body 4128 deform the tube 4110 while rotating clockwise by 90° such that the direction of the magnetic moments 4124a and 4128a coincide with the direction of the magnetic field of the external magnetic field 4200. The third magnetic body 4126 deforms the tube while rotating clockwise by 180° such that the direction of the magnetic moment 4126a coincides with the direction of the magnetic field of the external magnetic field 4200.

The tube 4110 may be bent to have an S shape by arranging the first to fifth magnetic bodies 4122, 4124, 4126, 4128, and 4130.

FIG. 29 is a view illustrating a magnetic tube system according to a fifth embodiment of the present invention.

Referring to FIG. 29, the magnetic tube system 4100 includes a tube 4100 and first to fifth magnetic bodies 4122, 4124, 4126, 4128, and 4130 inserted into the tube 4100.

The directions and magnitudes of the magnetic moments 4122a, 4124a, 4126a, 4128a, and 4130a of the first to fifth magnetic bodies 4122, 4124, 4126, 4128, and 4130 inserted into the tube 4100 of the magnetic tube system 4100A may be different.

The direction of the magnetic moment 4122a of the first magnetic body 4122 is opposite to the lengthwise direction X of the tube 4110, the direction of the magnetic moment 4124a of the second magnetic body 4124 may form an angle of 135° with the lengthwise direction of the tube 4110, the direction of the magnetic moment 4126a of the third magnetic body 4126 is perpendicular to the lengthwise direction X of the tube 4110, the direction of the magnetic moment 4128a of the fourth magnetic body 4128 may form an angle of 45° with the lengthwise direction of the tube 4110, and the direction of the magnetic moment 4130a of the fifth magnetic body 4130 is same as the lengthwise direction X of the tube 4110.

The magnitudes of the magnetic moments 4126a and 4130a of the third magnetic body 4126 and the fifth magnetic body 4130 are greater than those of the magnetic moments 4122a, 4124a, and 4128a of the first magnetic body 4122, the second magnetic body 4124, and the fourth body 4128.

FIG. 30 is a view illustrating a modification of the magnetic tube system according to the fifth embodiment of the present invention when an external magnetic field of a low intensity is applied to the magnetic tube system.

Referring to FIG. 30, the magnetic force of the external magnetic field 4200 may be applied in the same direction of the lengthwise direction X of the tube 4110 with the low intensity.

With the application of the external magnetic field 4200, a higher magnetic force and a higher magnetic torque are applied to the third magnetic body 4126 and the fifth magnetic body 4130, of which the magnitudes of the magnetic moments are relatively larger, as compared with the first magnetic body 4122, the second magnetic body 4124, and the fourth magnetic body 4128. Accordingly, the third magnetic field 4126 and the fifth magnetic body 4130 may be arranged in the direction of the magnetic force of the external magnetic field 4200.

In detail, the third magnetic body 4126 deforms the tube while rotating clockwise by 90° such that the direction of the magnetic moment 4126a coincides with the direction of the magnetic field of the external magnetic field 4200. The fifth magnetic body 4130 does not deform the tube 4110 as the direction of the magnetic moment 4130a coincides with the direction of the magnetic field of the external magnetic field 4200.

Meanwhile, a low magnetic torque and a low magnetic force are applied to the first magnetic body 4122, the second magnetic body 4124, and the fourth magnetic body 4128 from the external magnetic field 4200 due to the magnetic moment of a small magnitude. Accordingly, the first magnetic body 4122, the second magnetic body 4124, and the fourth magnetic body 4128 do not overcome the elasticity of the tube 4110 and are arranged in the direction of the magnetic force of the external magnetic field 4200.

FIG. 31 is a view illustrating a modification of the magnetic tube system according to the fifth embodiment of the present invention when an external magnetic field of a high intensity is applied to the magnetic tube system.

Referring to FIG. 31, the magnetic force of the external magnetic field 4200 may be applied in the same direction of the lengthwise direction X of the tube 4110 with a strong strength.

Unlike in FIG. 29, with the application of a strong external magnetic field 4200, a magnetic force and a magnetic torque are applied to the first to fifth magnetic bodies 4122, 4124, 4126, 4128, and 4130 such that the directions of the magnetic moments 4122a, 4124a, 4126a, 4128a, and 4130a coincide with the direction of the magnetic field of the external magnetic field.

In detail, the first magnetic body 4122 deforms the tube while rotating clockwise by 180° such that the direction of the magnetic moment 4122a coincides with the direction of the magnetic field of the external magnetic field 4200. The second magnetic body 4124 deforms the tube while rotating clockwise by 135° such that the direction of the magnetic moment 4124a coincides with the direction of the magnetic field of the external magnetic field 4200. The third magnetic body 4126 deforms the tube while rotating clockwise by 90° such that the direction of the magnetic moment 4126a coincides with the direction of the magnetic field of the external magnetic field 4200. The forth magnetic body 4128 deforms the tube while rotating clockwise by 45° such that the direction of the magnetic moment 4128a coincides with the direction of the magnetic field of the external magnetic field 4200. The fifth magnetic body 4130 does not deform the tube 4110 as the direction of the magnetic moment 4130a coincides with the direction of the magnetic field of the external magnetic field 4200.

In this way, the deformed form of the tube may be selected by varying the magnitudes of the magnetic moments of the magnetic bodies.

It has been identified in the various embodiments that the tube may be deformed to have various shapes as the directions and magnitudes of the magnetic moments of the magnetic bodies vary. The present invention is not limited to the above-described embodiments, and the directions and magnitudes of the magnetic moments may be variously changed according to the shape of the tube.

The above description is a simple exemplification of the technical spirit of the present disclosure, and the present disclosure may be variously corrected and modified by those skilled in the art to which the present disclosure pertains without departing from the essential features of the present disclosure.

Therefore, the disclosed embodiments of the present disclosure do not limit the technical spirit of the present disclosure but are illustrative, and the scope of the technical spirit of the present disclosure is not limited by the embodiments of the present disclosure. The scope of the present disclosure should be construed by the claims, and it will be understood that all the technical spirits within the equivalent range fall within the scope of the present disclosure.

INDUSTRIAL APPLICABILITY

The present invention relates to a magnetic field control system that may control a motion of an in-pipe movement apparatus, and may be used for control of a motion of an apparatus that may move in various pipe environments, such as tubular tissues of human bodies including blood vessels, digestive organs, and urethras, domestic pipes, and industrial pipes.

The invention claimed is:

1. A magnetic field control system comprising:
   a structure forming part configured to form a three-dimensional structure having an inner space;
   a magnetic field generating part extending from a specific location of the structure forming part, disposed to face a target area defined in the inner space, and configured to generate a magnetic field; and
   a power source part configured to supply electric power to the magnetic field generating part,
   wherein the magnetic field generating part includes a first magnetic field generating part and a second magnetic field generating part,
   wherein the power source part includes a first power source part and a second power source part,
   wherein the first magnetic field generating part includes:
      a first magnetic core extending from a specific location of the structure forming part;
      a first coil wound on the first magnetic core; and
      a first variable capacitor, one end of which is connected to an opposite end of the first coil and an opposite end of which is connected to the first power source part, and
   wherein the second magnetic field generating part includes:
      a second magnetic core extending from a specific location of the structure forming part;
      a second coil wound on the second magnetic core; and
      a second variable capacitor, one end of which is connected to an opposite end of the second coil and an opposite end of which is connected to the second power source.

2. The magnetic field control system of claim 1, wherein the first coil, the first variable capacitor, and the first power source part form a first closed circuit, and
   wherein a resonance frequency of the first closed circuit varies according to a capacitance of the first variable capacitor.

3. The magnetic field control system of claim 2, wherein the second coil, the second variable capacitor, and the second power source part form a second closed circuit, and
   wherein a resonance frequency of the second closed circuit varies according to a capacitance of the second variable capacitor.

4. The magnetic field control system of claim 3, wherein the capacitances of the first variable capacitor and the second variable capacitor are set to be the same or different.

5. The magnetic field control system of claim 1, wherein the first magnetic core and the second magnetic core are cylindrical magnetic bodies.

6. The magnetic field control system of claim 1, wherein each of the first variable capacitor and the second variable capacitor includes a plurality of capacitors connected in parallel to each other.

7. The magnetic field control system of claim 1, wherein a plurality of magnetic field generating parts are provided, and
   wherein each of the magnetic field generating parts includes:
      a plurality of magnetic cores extending from specific locations of the structure forming part;
      a plurality of coils wound on the plurality of magnetic cores, respectively; and
      a plurality of variable capacitors having ends of which are connected to opposite ends of the plurality of coils and opposite ends of which are connected to the power source part.

8. The magnetic field control system of claim 7, wherein a plurality of power source parts are provided to supply electric power to the plurality of coils, independently.

9. The magnetic field control system of claim 8, wherein among the plurality of coils, the plurality of variable capacitors, and the power source parts, a coil, a variable capacitor, and a power source part, which are connected to each other, form a closed circuit, and
   wherein a resonance frequency of the closed circuit varies according to the capacitance value of the variable capacitor.

10. The magnetic field control system of claim 7, wherein the three-dimensional structure is a rectangular parallelepiped or a regular hexahedron, and the plurality of cores extend from apexes of the rectangular parallelepiped or the regular hexahedron to face the target area.

11. The magnetic field control system of claim 7, wherein the three-dimensional structure is a sphere,
   wherein the structure forming part includes two circular magnetic core rings coupled to each other such that planes defined in the interior of the structure forming part are perpendicular to each other and the centers thereof coincide with each other, and
   wherein the plurality of magnetic cores are disposed to face the target area from specific locations of the two circular magnetic core rings.

* * * * *